US008008282B2

(12) United States Patent
Serhan et al.

(10) Patent No.: US 8,008,282 B2
(45) Date of Patent: Aug. 30, 2011

(54) LIPOXIN ANALOGS AS NOVEL INHIBITORS OF ANGIOGENESIS

(75) Inventors: Charles N. Serhan, Needham, MA (US); Iolanda M. Fierro, Rio de Janeiro (BR)

(73) Assignee: The Brigham & Women's Hospital, Inc., Boston, MA (US)

( * ) Notice: Subject to any disclaimer, the term of this patent is extended or adjusted under 35 U.S.C. 154(b) by 58 days.

(21) Appl. No.: 11/222,458

(22) Filed: Sep. 8, 2005

(65) Prior Publication Data

US 2006/0009521 A1    Jan. 12, 2006

Related U.S. Application Data

(62) Division of application No. 10/615,361, filed on Jul. 8, 2003, now abandoned, which is a division of application No. 10/086,609, filed on Mar. 1, 2002, now Pat. No. 6,627,658.

(60) Provisional application No. 60/272,931, filed on Mar. 2, 2001.

(51) Int. Cl.
*A01N 37/30* (2006.01)
*A61K 31/205* (2006.01)

(52) U.S. Cl. ........................... 514/183; 514/559
(58) Field of Classification Search ............ 514/183, 514/559
See application file for complete search history.

(56) References Cited

U.S. PATENT DOCUMENTS

| | | | |
|---|---|---|---|
| 4,560,514 A | 12/1985 | Samuelsson et al. | |
| 4,576,758 A | 3/1986 | Morris | |
| 4,780,281 A | 10/1988 | Marnett et al. | |
| 5,049,681 A | 9/1991 | Sato | |
| 5,079,261 A | 1/1992 | Serhan et al. | |
| 5,322,699 A | 6/1994 | Wright et al. | |
| 5,441,951 A | 8/1995 | Serhan | |
| 5,648,512 A | 7/1997 | Serhan | |
| 5,650,435 A | 7/1997 | Madara et al. | |
| 5,750,354 A | 5/1998 | Simchowitz et al. | |
| 5,837,283 A | 11/1998 | McDonald | |
| 6,048,897 A * | 4/2000 | Serhan ................... | 514/560 |
| 6,100,296 A | 8/2000 | Madara et al. | |
| 6,177,468 B1 | 1/2001 | Madara et al. | |
| 6,316,648 B1 | 11/2001 | Serhan | |
| 6,329,425 B1 | 12/2001 | Madara et al. | |
| 6,387,953 B1 | 5/2002 | Serhan | |
| 6,627,658 B2 | 9/2003 | Serhan et al. | |
| 6,653,493 B2 | 11/2003 | Serhan et al. | |
| 2002/0168361 A1 | 11/2002 | Kelly | |
| 2004/0053998 A1 | 3/2004 | Serhan et al. | |

FOREIGN PATENT DOCUMENTS

| | | |
|---|---|---|
| JP | 62-198677 | 9/1987 |
| JP | 63-88153 | 4/1988 |
| JP | 1-228994 | 9/1989 |
| JP | 3-227922 | 10/1991 |
| WO | WO 94/29262 | 12/1994 |
| WO | WO 95/01179 | 1/1995 |
| WO | WO 98/11049 | 3/1998 |
| WO | WO 00/54767 | 9/2000 |
| WO | WO 00/55109 | 9/2000 |
| WO | WO 01/70664 | 9/2001 |

OTHER PUBLICATIONS

Ather et. al., Wound Management—Developmentts in treatment options, European Dermatology review, 2006, 59-60.*
Kramer, Effect of zpovidone-iodine on wound healing: a review, Journal of vascular nursing, 1999, 27:17-21.*
Krishnan, Current Anaesthesia and critical care (2006) 17:21-27.*
Ganz T., et al., "Antimicrobial Peptides of Phagocytes and Epithelia", Seminars in Hematology, Oct. 1997, vol. 34, No. 4, pp. 343-354, XP009009059.
Elsbach P. et al., "Role of the Bactericidal/Permeability-Increasing Protein in Host Defense", Current Opinion in Immunology, Feb. 1998, vol. 10, No. 1, pp. 45-49, XP002238031.
Canny Geraldine et al., "Lipid Mediator-Induced Expression of Bactericidal/Permeability-Increasing Protein (BPI) in Human Mucosal Epithelia", Proceedings of the National Academy of Sciences of the United States of America, Mar. 2002, vol. 99, No. 6, pp. 3902-3907, XP002238032.
Levy Ofer, "Therapeutic Potential of the Bactericidal/Permeability-Increasing Protein", Expert Opinion of Investigational Drugs, Feb. 2002, vol. 11, No. 2, pp. 159-167, XP001147178.
Levy Ofer, "A Neutrophil-Derived Anti-Infective Molecule: Bactericidal/Permeabilty-Increasing Protein", Antimicrobial Agents and Chemotherapy, United States Nov. 2000, pp. 2925-2931, XP002238033.
Levy Ofer, "Antimicrobial Proteins and Peptides of Blood: Templates for Novel Antimicrobial Agents", Blood, Oct. 15, 2000, vol. 96, No. 8, pp. 2664-2672, XP002238034.
Takano, T. et al., Neutrophil-meidated Changes in Vascular Permeability are Inhibited by Topical Application of Aspirin-triggered 15-epi-lipoxin A4 and Novel Lipoxin B4 Stable Analogues:, *J. Clin. Invest.*, vol. 101, No. 4, 1998, pp. 819-826.
Corey, E.J. et al., "On the Synthesis and Structure of Lipoxin B", *Tetrahedron Letters*, vol. 26, No. 16, 1985, pp. 1919-1922.
Samuelsson, B., "An Elucidation of Arachidonic Acid Cascade Discovery of Prostaglandins, Thromboxane and Leukotrienes", *Drugs*, vol. 33, Supp. 1, 1987, pp. 209.
Nash, S. et al.,"Effects of Polymorphonuclear Leukocyte Transmigration on the Barrier Function of Cultured Intestinal Epithelial Monolayers", *J. Clin. Invest.*, vol. 80, 1987, pp. 1104-1113.
Popov, G. K., et al., "Effect of Lipoxin B on Colony-Forming Ability of Human Peripheral Blood Mononuclears in a Diffusion Chamber", *Chelyabinsk Medical Institute*, Department of Pathophysiology and Section of Human Cardiovascular Pathology. Translated from Byulleten' Eksperimental' noi Biologii i Meditsiny, vol. 107, No. 1, 1989, pp. 80-83.

(Continued)

*Primary Examiner* — Marcos L Sznaidman
(74) *Attorney, Agent, or Firm* — Colin L. Fairman; Scott D. Rothenberger; Fulbright & Jaworski

(57) ABSTRACT

The present invention is directed to methods for the prevention or inhibition of angiogenesis. The method is accomplished by the administration of an effective amount of 15-epi-16-(para-fluoro)-phenoxy-lipoxin $A_4$, $LXA_4$, 15-epi-$LXA_4$ or 15-R/S-methyl, $LXA_4$ and pharmaceutically acceptable salts, esters, amides, carboxylic acids, or prodrugs thereof, to a subject in need thereof. As a consequence of the action of the therapeutic agent, angiogenesis is prevented or inhibited in the subject.

1 Claim, 7 Drawing Sheets

OTHER PUBLICATIONS

Nicolaou, K.C., et al., "Identification of a novel 7-cis-11-trans-lipoxin A4 generated by human neutrophils: total synthesis, spasmogenic activities and comparison with other geometric isomers of lipoxins A4 and B4", *Biochimica et Biophysica Acts*, No. 1003, 1989, pp. 44-53.

Nicolaou, K.C. et al., "Total Synthesis of Novel Geometric Isomers of Lipoxin A4 and Lipoxin B4", *Reprinted from the Journal of Organic Chemistry*, vol. 54, 1989, pp. 5527-5535.

Nigam, S., et al., "Lipoxin A4 and Lipoxin B4 Stimulate the Release but Not the Oxgenation of Arachidonic Acid in Human Neutrophils: Dissociation Between Lipid Remodeling and Adhesion", *Journal of Cellular Physiology*, vol. 143, 1990, pp. 512-523.

Fiore, S., et al., "The Lipoxin Biosynthetic Circuit and Their Actions with Human Neutrophils", *Advances in Experimental Medicine and Biology*, vol. 314, 1991, pp. 109-132.

Pettitt, T.R., et al. "Synthesis of Lipoxins and Other Lipoxygenase Products by Macrophages from the Rainbow Trout, Oncorhynchus mykiss", *The Journal of Biological Chemistry*, vol. 266, No. 14, 1991, pp. 8720-8726.

Parkos, C.A., et al., "Neutrophil Migration across a Cultured Intestinal Epithelium", *J. Clin. Invest.*, vol. 88, 1991, pp. 1605-1612.

Lee, T.H., et al. "Inhibition of Leukotriene B4-Induced Neutrophil Migration by Lipoxin A4: Structure-Function Relationships", *Biochemical and Biophysical Research Communications*, vol. 180, No. 3, 1991, pp. 1416-1421.

Serhan, C., "Lipoxins: Eicosanoids Carrying Intra- and Intercellular Messages", *Journal of Bioenergetics and Biomembranes*, vol. 23, No. 1, 1991, pp. 105-122.

Brady, H.R., et al., "Leukotrienes stimulate neutrophil adhesion to mesangial cells: modulation with lipoxins", *American Journal Physiology*, vol. 259, 1990, pp. F809-F815.

Nicolaou, K.C., et al., "Lipoxins and Related Eicosanoids: Biosynthesis, Biological Properties, and Chemical Synthesis", *Angew, Chem. Int. Ed. Engl.*, vol. 30, 1991, pp. 1100-1116.

Badr, K.F., "15-Lipoxygenase products as leukotriene antagonists: Therapeutic potential in glomerulonephritis", *Kidney International*, vol. 42, Supp. 38, 1991, pp. S101-S108.

Fiore, S., et al., "Lipoxin Recognition Sites", *The Journal of Biological Chemistry*, vol. 267, No. 23, 1992, pp. 16168-16176.

Parkos, C.A., et al., "Neutrophil Migration Across a Cultured Epithelial Monolayer Elicits a Biphasic Resistance Response Representing Sequential Effects on Transcellular and Paracellular Pathways", *The Journal of Cell Biology*, vol. 117, No. 4, 1992, pp. 757-764.

Madara, J.L., et al., "A Simple Approach to Measurement of Electrical Parameters of Cultured Epithelia Monolayers: Use in Assessing Neutrophil-Epithelial Interactions", *J. Tiss. Cult. Meth.*, vol. 14, 1992, pp. 209-216.

Kathoh, T., et al., "Renal hemodynamic actions of lipoxins in rats: a comparative physiological study", *American Journal Physiology*, vol. 263, 1992, pp. F436-F442.

Folkman, J., et al., "Angiogensis", *J. Biol. Chem.*, 267, 1992, pp. 10931-10934.

Lederman, S. et al., "Identification of a Novel Surface Protein on Activated CD4+ T Cells That Induces Contact-dependent B Cell Differentiation (Help)", *J. Exp. Med.*, vol. 175, 1992, pp. 1091-1101.

Hla, T.A., et al. "Cyclooxygenase Gene Expression in Inflammation and Angiogensis". *Annals N.Y. Acad. Sci.*, vol. 696, 1993, pp. 197-204.

Madara, J.L., et al. "5'-Adenosine Monophosphate is the Neutrophil-dervied Paracrine Factor that Elicits Chloride Secretion from T84 Intestinal Epithelial Cell Monolayers", *J. Clin. Invest.*, vol. 91, 1993, pp. 2320-2325.

Fiore, S. et al., "Induction of Functional Lipoxin A4 Receptors in HL-60 Cells", *Blood*, vol. 9, No. 12, 1993, pp. 3395-3403.

Mizukami, Y. et al., "ω-Hydroxylation of lipoxin B4 by human neutrophil microsomes: identification of ω-hydroxy metabolite of lipoxin B4 and catalysis by leukotriene B4 ω-hydroxylase (cytochrome P-450LTBω)", *Biochimica et Biophysica Acta*, No. 1168, 1993, pp. 87-93.

Claria, J. et al., "Aspirin triggers previously undescribed bioactive eicosanoids by Human endothelial cell-leukocyte interacions", *Proc. Natl. Acad. Sci. USA* 92, No. 21, 1995, pp. 9475-9479.

Marshall, N.J. et al., "A Critical Assessment of the Use of Microculture Tetrazolium Assys to Measure Cell Growth and Function", *Growth Regulation*, 5, 1995, pp. 69-84.

Folkman, J., "Angiogensis in cancer, vascular, rheumatorid and other disease", *Nature Medicine*, vol. 1. No. 1, 1995, pp. 27-31.

Marcus, A.J., "Aspirin as Prophylaxis Against Colorectal Cancer", *New Eng. J. Med.*, vol. 333, No. 10, 1995, pp. 636-638.

Colville-Nash, P.R., et al, "The Pharmacological Modulation of Angiogensis in Chronic Granulomatous Inflammation", *J. Pharmacol.*, vol. 274, No. 3, 1995, pp. 1463-1472.

Maddox, J.F., et al., "Lipoxin A4 and B4 Are Potent Stimuli for Human Monocyte Migration and Adhesion: Selective Inactivation by Dehydrogenation and Reduction", *J. Exp. Med.*, vol. 183, 1996, pp. 137-146.

Stoltz, R.A. et al., "The role of NF-κB in the angiogenic response to coronary microvessel endothelial cells", *Proc. Natl. Acad. Sci. USA*, vol. 93, 1996, pp. 2832-2837.

Claria, J. et al., "Aspirin-Triggered Lipoxins (15-epi-LX) Are Generated by the Human Lung Adenocarcinoma Cell Line (A549)—Neutrophil Interactions and Are Potentin Inhibitors of Cell Proliferation", *Molecular Medicine*, vol. 2, No. 5, 1996, pp. 583-596.

Papayianni, A. et al., "Lipoxin A4 and B4 Inhibit Leukotriene-Stimulated Interactions of Human Neutrophils and Endothelial Cells", *J. Immunology*, vol. 156, 1996, pp. 2264-2272.

Romano, M. et al, "Activation of Human Monocytes and the Acute Monocytic Leukemia Cell Line (THP-1) by Lipoxins Involves Unique Signaling Pathways for Lipoxin A4 Versus Lipoxin B4", *J. Immunology*, vol. 157, 1996, pp. 2149-2154.

Serhan, C., "Lipoxins and Novel Aspirin-Triggered 15-epi-Lipoxins (ATL): A Jungle of Cell-Cell Interactions or a Therapeutic Opportunity?", *Prostaglandins*, vol. 53, No. 2, 1997, pp. 107-137.

Takano, T. et al., "Aspirin-Triggered 15-epi-Lipoxin A4 (LXA4) and LXA4 Stable Analogs are Potent Inhibitors of Acute Inflammation: Evidence for Anti-inflammatory Receptors", *J. Exp. Med.*, vol. 185, No. 9, 1997, pp. 1693-1704.

Hoper, M.M., et al., "Prostaglandins Induce Vascular Endothelial Growth Factor in a Human Monocytic Cell Line and Rate Lungs via cAMP", *Am. J. Respir. Cell. Mol. Biol.*, vol. 17, 1997, pp. 748-756.

Gronert, K. et al, "Characterization of Human Neutrophil and Endothelial Cell Ligand-Operated Extracellular Acidification Rate by Microphysiometry: Impact of Reoxygenation", *J. Pharmacol. Exp. Therap.*, vol. 285, No. 1, 1998, pp. 252-260.

Maddox, J. F. et al., "Lipoxin B4 regulates human monocyte/neutrophil adherence and motility: design of stable lipoxin B4 analogs with increased biologic activity", *The FASEB Journal*, vol. 12, 1998, pp. 487-494.

Gewirtz, A.T. et al., "Pathogen-induced Chemokine Secretion from Model Intestinal Epithelium is Inhibited by Lipoxin A4 Analogs", *J. Clin. Invest.*, vol. 101, No. 9, 1998, pp. 1860-1869.

Chiang, N. et al., "Aspirin-Triggered 15-epi-Lipoxin A4 (ATL) Generation by Human leukocytes and Murine Peritonitis Exudates: Development of a Specific 15-epi-LXA4, ELISA1", *J. Pharmacol. Exp. Therap.*, vol. 287, No. 2, 1998, pp. 779-790.

Serhan, C., "Lipoxins and Aspirin-Triggered 15-epi-Lipoxins", *Inflammation: Basic Principles and Clinical Correlates*, 3rd ed. 1999, pp. 373-385.

Arenberg, D.A. et al, "Angiogensis", *Inflammation: Basic Principles and Clinical Correlates*, 3rd ed. 1999, pp. 851-864.

Gupta, K. et al., "VEGF Prevents Apoptosis of Human Microvascular Endothelial Cells via Opposing Effectson MAPK/ERK and SAPK/JNK Signaling", *Experimental Cell Research*, vol. 247, No. 2, 1999, pp. 495-504.

Kelavkar, U.P. et al., "Effects of mutant p53 expression on human 15-lipoxygenase-promoter activity and murine 12/15-lipoxygenase gene expression: Evidence that 15-lipoxygenase is a mutator gene", *Proc. Natl. Acad. Sci. USA*, vol. 96, 1999, pp. 4378-4383.

Eliceiri, B.P. et al., "The role of αv integrins during angiogenesis: insights into potential mechanisms of action and clinical development", *J. Clin. Invest.*, vol. 103, No. 9, 1999, pp. 1227-1230.

Hachicha, M. et al., "Lipoxin (LX) A4 and Aspirin-Triggered 15-epi-LXA4 Inhibit Tumor Necrosis Factor 1α-initiated Neutrophil Responses and Trafficking: Regulators of Cytokine-Chemokine Axis", *J. Exp. Med.*, vol. 189. No. 12, 1999, pp. 1923-1929.

Clish, C.B. et al., "Local and systemic delivery of a stable aspirin-triggered lipoxin prevents neutrophil recruitment in vivo", *Proc. Natl. Acad. Sci. USA*, vol. 96, 1999, pp. 8247-8252.

Munger, K.A. et al., "Transfection of rat kidney with human 15-lipoxygenase suppresses inflammation and preserves function in experimental glomerulonephritis", *Proc. Natl. Acad. Sci. USA*, vol. 96, No. 23, 1999, pp. 13375-13380.

Masferrer, J.L., et al, "COX-2 Inhibitors a New Classof Antiangiogenic Agents", *Annals. N.Y. Acad. Sci.*, vol. 889. 1999, pp. 84-86.

Jones, M.K. et al., "Inhibition of angiogenesis by nonsteroidal anti-inflammatory drugs: Insight into mechanisms and implications for cancer growth and ulcer healing", *Nature Medicine*, vol. 5, No. 12, 1999, pp. 1418-1423.

Serhan, C.N. et al., "Formation of Endogenous "Antiinflammatory" Lipid Mediators by Transcellular Biosynthesis", *Am. J. Respir. Crit. Care Med.*, vol. 161, 2000, pp. S95-S101.

Sodin-Semrl, S. et al., "Lipoxin A4 Inhibits IL-1B-Induced IL-6, IL-8, and Matrix Metalloproteinase-3 Production in Human Synovial Fibroblasts and Enhances Synthesis of Tissue Inhibitors of metalloproteinases", *J. Immunolog.*, vol. 164, No. 5, 2000, pp. 2660-2666.

Sanak, M. et al., "Aspirin-tolerant asthmatics generate more lipoxins than aspirin-intolerant asthmatics", *Eur. Respir. J.*, vol. 16, 2000, pp. 44-49.

Nie, D. et al., "Eicosanoid regulation of angiogenesis: role of endothelial arachidonate 12-lipoxygenase", *Blood*, vol. 95. No. 7, 2000, pp. 2304-2311.

McMahon, B. et al., "Lipoxin A4 Antagonizes the Mitogenic Effects of Leukotriene D4 in Human Renal Mesangial Cells", *J. Biolog. Chem.*, vol. 275. No. 36, 2000, pp. 27566-27575.

Vane, J., "Aspirin and other anti-inflammatory drugs", *Thorax*, vol. 55, Supp. 2, 2000, pp. S3-S9.

Chiang, N. et al., "Lipoxin A4 Receptor", Cytokine Reference, Academic Press, London, 2001, pp. 2199-2233.

Gronert, K. et al., "Short Communication Selectivity of Recombinant Human Leukotriene D4, Leukotriene B4, and Lipoxin A4 Receptors with Aspirin-Triggered 15-epi-LXA4 and Regulation of Vascular and Inflammatory Responses", *Am. J. Pathol.*, vol. 159, No. 1, 2001, pp. 3-9.

Stacker, S.A. et al., "VEGF-D promotes the metastatic spread of tumor cells via the lymphatics", *Nature Medicine*, vol. 7, No. 2, 2001, pp. 186-191.

Skobe, M. et al., "Induction of tumor lymphangiogenesis by VEGF-C promotes breast cancer metastasis", *Nature Medicine*, vol. 7, No. 2, 2001, pp. 192-198.

Makinen, T. et al., "Inhibition of lymphangiogenesis with resulting lymphedema in transgenic mice expressing soluble VEGF receptor-3", *Nature Medicine*, vol. 7, No. 2, 2001, pp. 199-205.

Serhan, C.N. et al., "Unorothox routes to prostanoid formation: new twists in cyclooxygenase-initiated pathways", *J. Clin. Invest.*, vol. 107, No. 12, 2001, pp. 1481-1489.

Serhan, C. et al., "Design of Lipoxin A4 Stable Analogs that Block Transmigration and Adhesion of Human Neutrophils", *Biochemistry*, vol. 34 No. 44, 1995, pp. 14609-14615.

Maddox, J.F. et al., "Lipoxin A4 Stable Analogs are Potent Mimetics that Stimulate Human Monocytes and THP-1 Cells via a G-protein-linked Lipoxin A4 Receptor", *The Journal of Biological Chemistry*, vol. 272 No. 11, 1997, pp. 6972-6978.

XP008017720, I. Fierro et al., "A Novel Inhibitor of Angiogenesis: Aspirin-Triggered 15-R Lipoxin A4", FASEB Journal, vol. 15, No. 5, 2001, pp. A949.

XP002244851, C.N. Serhan, et al., "Current Inflammation Research Series: Molecular and Cellular Basis of Inflammation", Humana Press Inc., 1999, pp. xii-338p.

* cited by examiner

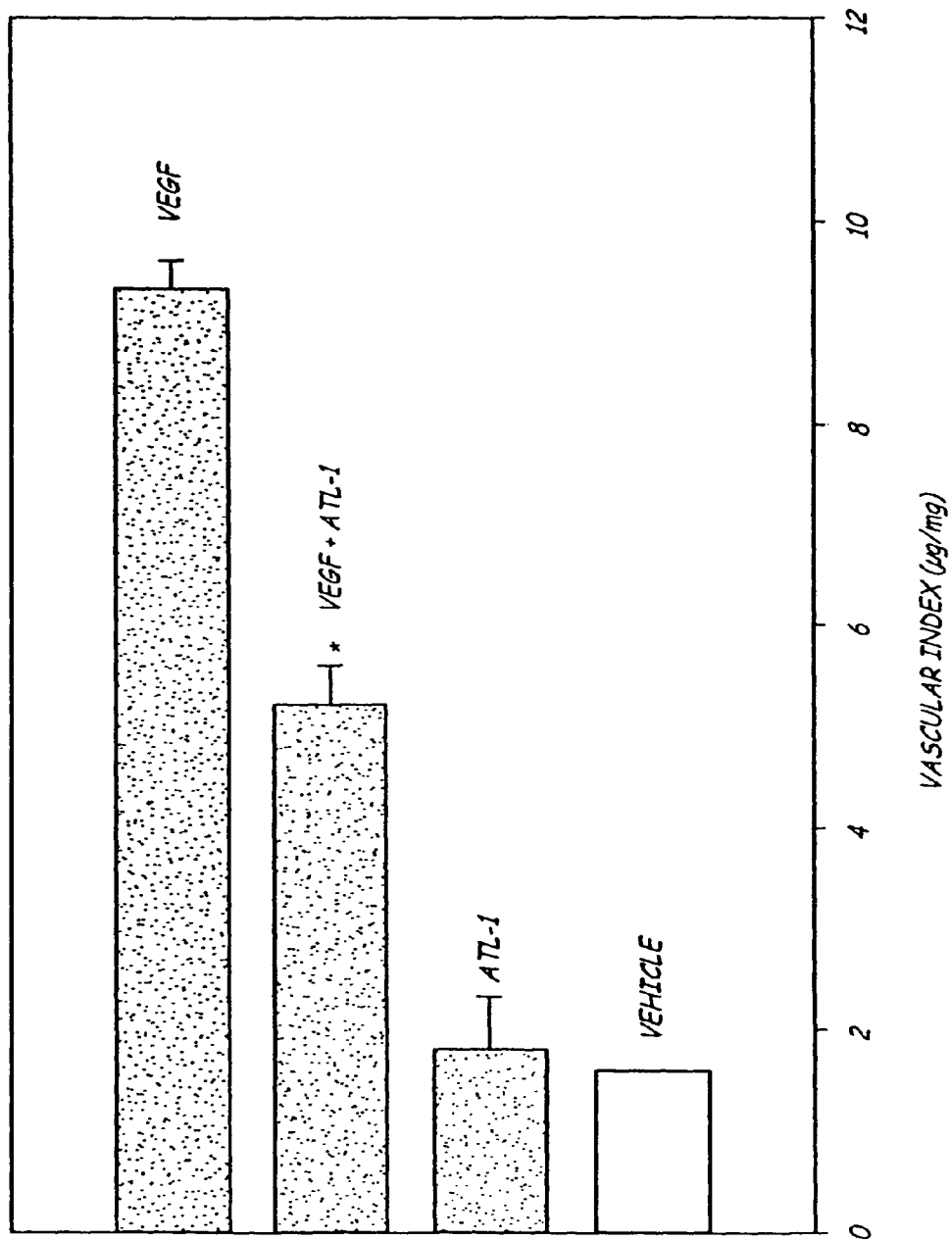

LIPOXIN ANALOGS AS NOVEL INHIBITORS OF ANGIOGENESIS

CROSS REFERENCE TO RELATED APPLICATION(S)

This application is a divisional of and claims priority to U.S. application Ser. No. 10/615,361, filed Jul. 8, 2003, now abandoned which is a divisional application of U.S. patent application Ser. No. 10/086,609, filed Mar. 1, 2002, now U.S. Pat. No. 6,627,658, which claims benefit of U.S. Provisional Patent Application Ser. No. 60/272,931, filed Mar. 2, 2001.

STATEMENT REGARDING FEDERALLY SPONSORED RESEARCH

The U.S. government may have rights in this invention pursuant to National Institute of Health Grant Nos. GM38765 and P01-DE13499.

BACKGROUND OF THE INVENTION

Angiogenesis is a fundamental process by which new capillaries are formed from existing blood vessels. This process plays important roles in physiological events such as formation of the corpus luteum, development of the embryo and wound healing, including recovery from both myocardial ischemia and peptic ulcer (1). Unregulated growth of blood vessels can contribute to tissue injury in a large number of diseases such as arthritis, diabetes, and tumor progression (2). Endothelial cells are normally quiescent and are activated during the angiogenic response. Upon stimulation, endothelial cells can degrade their basement membrane and proximal extracellular matrix, migrate directionally, then divide and organize into functional capillaries invested by a new basal lamina (3).

There is a growing body of evidence demonstrating that the angiogenic switch is regulated by the net balance between positive and negative regulators of new capillary growth (2). Persistence of neovascularization requires a pro-angiogenic environment, with the expression of angiogenic factors outweighing that of angiostatic factors. A range of peptides can influence this balance, including mitogenic factors such vascular endothelial growth factor (VEGF) (3), nonmitogenic factors (selected cytokines, CXC chemokines), and internal peptide fragments of angiostatin and endostatin (3). Certain eicosanoids also have potent biologic actions on vascular endothelial cells. In rabbits, $PGE_2$, $PGR_{2\alpha}$, and prostacylin ($PGI_2$) stimulate angiogenesis where prostaglandin E series, in particular $PGE_1$, is most potent. $PGE_2$ is a potent inducer of VEGF expression in synovial fibroblasts. In addition to its known vasodilator and antiplatelet properties, $PGI_2$ can also induce VEGF gene expression and protein synthesis (4).

It was recently reported that 12-lipoxygenase activity and one of its products, 12(S)-HETE, is required for angiogenic responses (5), and that P450-derived 12R-HETE stimulates angiogenesis via NF-kB (6). The cyclooxygenase-2 (COX-2) gene in endothelial cells is rapidly upregulated by several growth factors as well as inducers of angiogenesis (7). Along these lines, results using three different endothelial cell models show that COX-2 is an essential component of angiogenesis, at least in vitro (8). Nonsteroidal anti-inflammatory drugs such as aspirin (ASA) have been implicated in the prevention of certain cancers such as lung and colon cancer (9, 10) that might be related to ASA's ability to reduce angiogenesis (7).

A need therefore exists, for compositions and methods to prevent angiogenesis that are directed toward the disease process, such that angiogenesis is prevented or inhibited physiologically. A need also exists for compositions and methods that induce angiogenesis in tissue that is lacking the requisite or essential physiological requirements for sustainability.

SUMMARY

Proliferative states such as chronic inflammation, ischemic diseases and cancer are often accompanied by intense angiogenesis, a highly orchestrated process involving vessel sprouting, endothelial cell migration, proliferation and maturation. Aspirin-triggered lipoxins (ATL), the 15R enantiomeric counterparts of lipoxins (LXs), are endogenous mediators generated during multicellular responses that display potent immunomodulatory actions. Surprisingly, it has been discovered that LXs, ATLs, and more specifically, the ATL stable analogs, 15-epi-16-(para-fluoro)-phenoxy-lipoxin $A_4$ (denoted ATL-1), $LXA_4$, 15-epi-$LXA_4$ and 15-R/S-methyl, $LXA_4$ are potent inhibitors of angiogenesis. For example, ATL-1, $LXA_4$, 15-epi-$LXA_4$ and 15-R/S-methyl, $LXA_4$ each inhibited endothelial cell proliferation in the 1-10 nM range by ~50% in cells stimulated with either vascular endothelial growth factor (VEGF) at 3 ng/ml or leukotriene $D_4$ (10 nM). In addition, ATL-1 (in a 10-100 nM range) inhibited VEGF (3 ng/ml)-induced endothelial cell chemotaxis. In a granuloma in vivo model of inflammatory angiogenesis, ATL-1 treatment (10 μg/mouse) reduced by ~50% the angiogenic phenotype, as assessed by both vascular casting and fluorescence. Together, these results identified a novel and potent previously unappreciated action of aspirin-triggered 15-epi-LX.

In one aspect, the present invention pertains to methods for the prevention, reduction or inhibition of angiogenesis. The method is accomplished by the administration of an effective amount of $LXA_4$ and analogs thereof, such as 15-R/S methyl, $LXA_4$, and pharmaceutically acceptable salts, esters, amides or prodrugs thereof, to a subject in need thereof. As a consequence of the action of the therapeutic agent, angiogenesis is prevented or inhibited in the subject.

In another aspect, the present invention also pertains to methods for the prevention or inhibition of angiogenesis. The method is accomplished by the administration of an effective amount of an aspirin triggered lipoxin (ATL) (15-epi-$LXA_4$, such as 15-epi-16-(para-fluoro)-phenoxy-lipoxin $A_4$ (ATL-1)), and pharmaceutically acceptable salts, esters, amides or prodrugs thereof, to a subject in need thereof. As a consequence of the action of the therapeutic agent, angiogenesis is prevented or inhibited in the subject.

In still another aspect, the present invention pertains to methods for the prevention or inhibition of solid tumor tissue growth undergoing neovascularization in a subject. The method is accomplished by the administration of an effective amount of an aspirin triggered lipoxin (ATL) (15-epi-$LXA_4$, such as 15-epi-16-(para-fluoro)-phenoxy-lipoxin $A_4$ (ATL-1)), and pharmaceutically acceptable salts, esters, amides or prodrugs thereof, to a subject in need thereof, to a subject in need thereof.

In another aspect, the present invention pertains to methods for the prevention or inhibition of solid tumor tissue growth undergoing neovascularization in a subject. The method is accomplished by the administration of an effective amount of $LXA_4$ and analogs thereof, such as 15-R/S methyl, $LXA_4$, and pharmaceutically acceptable salts, esters, amides or prodrugs thereof, to a subject in need thereof.

In yet another aspect, the present invention is directed to methods to inhibit or prevent neovascularization from occurring in a subject. The method is accomplished by the administration of an effective amount of LXA$_4$ and analogs thereof, such as 15-R/S methyl, LXA$_4$, and pharmaceutically acceptable salts, esters, amides or prodrugs thereof, to a subject in need thereof.

In yet another aspect, the present invention is directed to methods to inhibit or prevent neovascularization from occurring in a subject. The method is accomplished by the administration of an effective amount of an aspirin triggered lipoxin (ATL) (15-epi-LXA$_4$, such as 15-epi-16-(para-fluoro)-phenoxy-lipoxin A$_4$ (ATL-1)), and pharmaceutically acceptable salts, esters, amides or prodrugs thereof, to a subject in need thereof.

The invention is also directed to methods for treating a subject in which neovascularization is occurring in retinal tissue. The neovascularization in the retinal tissue can be prevented or inhibited by administering an effective amount of LXA$_4$ and analogs thereof, such as 15-R/S methyl, LXA$_4$, and pharmaceutically acceptable salts, esters, amides or prodrugs thereof, to a subject in need thereof.

The present invention is further directed to methods for treating a subject in which neovascularization is occurring in retinal tissue. The neovascularization in the retinal tissue can be prevented or inhibited by administering an effective amount of an aspirin triggered lipoxin (ATL) (15-epi-LXA$_4$, such as 15-epi-16-(para-fluoro)-phenoxy-lipoxin A$_4$ (ATL-1)), and pharmaceutically acceptable salts, esters, amides or prodrugs thereof, to a subject in need thereof.

The invention is further directed to methods for treating a subject for restenosis in tissue wherein smooth muscle cell migration occurs following angioplasty. The restenosis can be prevented or inhibited by administering an effective amount of LXA$_4$ and analogs thereof, such as 15-R/S methyl, LXA$_4$, and pharmaceutically acceptable salts, esters, amides or prodrugs thereof, to a subject in need thereof.

The invention is directed to methods for treating a subject for restenosis in tissue wherein smooth muscle cell migration occurs following angioplasty. The restenosis can be prevented or inhibited by administering an effective amount of an aspirin triggered lipoxin (ATL) (15-epi-LXA$_4$, such as 15-epi-16-(para-fluoro)-phenoxy-lipoxin A$_4$ (ATL-1)), and pharmaceutically acceptable salts, esters, amides or prodrugs thereof, to a subject in need thereof.

In still another embodiment, the invention pertains to methods of reducing blood supply to tissue required to support new growth of the tissue in a subject. This reduction or elimination of new undesired growth of tissue can be accomplished by the administration of a composition comprising an effective amount of LXA$_4$ and analogs thereof, such as 15-R/S methyl, LXA$_4$, and pharmaceutically acceptable salts, esters, amides or prodrugs thereof, to a subject in need thereof.

The invention further pertains to methods of reducing blood supply to tissue required to support new growth of the tissue in a subject. This reduction or elimination of new undesired growth of tissue can be accomplished by the administration of a composition comprising an effective amount of an aspirin triggered lipoxin (ATL) (15-epi-LXA$_4$, such as 15-epi-16-(para-fluoro)-phenoxy-lipoxin A$_4$ (ATL-1)), and pharmaceutically acceptable salts, esters, amides or prodrugs thereof, to a subject in need thereof.

Further, the present invention pertains to methods for the prevention, diminishment or inhibition the production of new vessels in a subject associated with or stimulated by the production or release of VEGF. The method is accomplished by the administration of an effective amount of a therapeutic agent, including LXA$_4$ and analogs thereof, such as 15-R/S methyl, LXA$_4$, and pharmaceutically acceptable salts, esters, amides or prodrugs thereof, to a subject in need thereof. Alternatively, an effective amount of an aspirin triggered lipoxin (ATL) (15-epi-LXA$_4$, such as 15-epi-16-(para-fluoro)-phenoxy-lipoxin A$_4$ (ATL-1)), and pharmaceutically acceptable salts, esters, amides or prodrugs thereof can be utilized. As a consequence of the action of the therapeutic agent, growth of new vessels associated with the production of VEGF is prevented or inhibited and thus the growth of endothelial cells in the subject. For example, VEGF is associated with tumor genesis, lymphoangiogenesis and proliferative disorders. The invention therefore, can be used to inhibit, reduce or prevent metasasis of tumors.

Surprisingly, configurational isomers of LXA$_4$, LXA$_4$ analogs and ATL analogs, LXB$_4$ and LXB$_4$ analogs and pharmaceutically acceptable salts, esters, amides or prodrugs thereof, provide the opposite effects with regard to revascularization of tissue by the above-identified compounds of the invention. That is, it has been surprisingly discovered that LXB$_4$ and LXB$_4$ analogs have the ability to stimulate regeneration and ingrowth of vascular or epithelial tissue in tissues that are in need of such stimulation. This is especially important in tissue grafting, tissue engineering and prosthetic group sites of attachment.

BRIEF DESCRIPTION OF THE DRAWINGS

The invention will be more fully understood from the following detailed description taken in conjunction with the accompanying drawings, in which.

DETAILED DESCRIPTION

Figure 1:
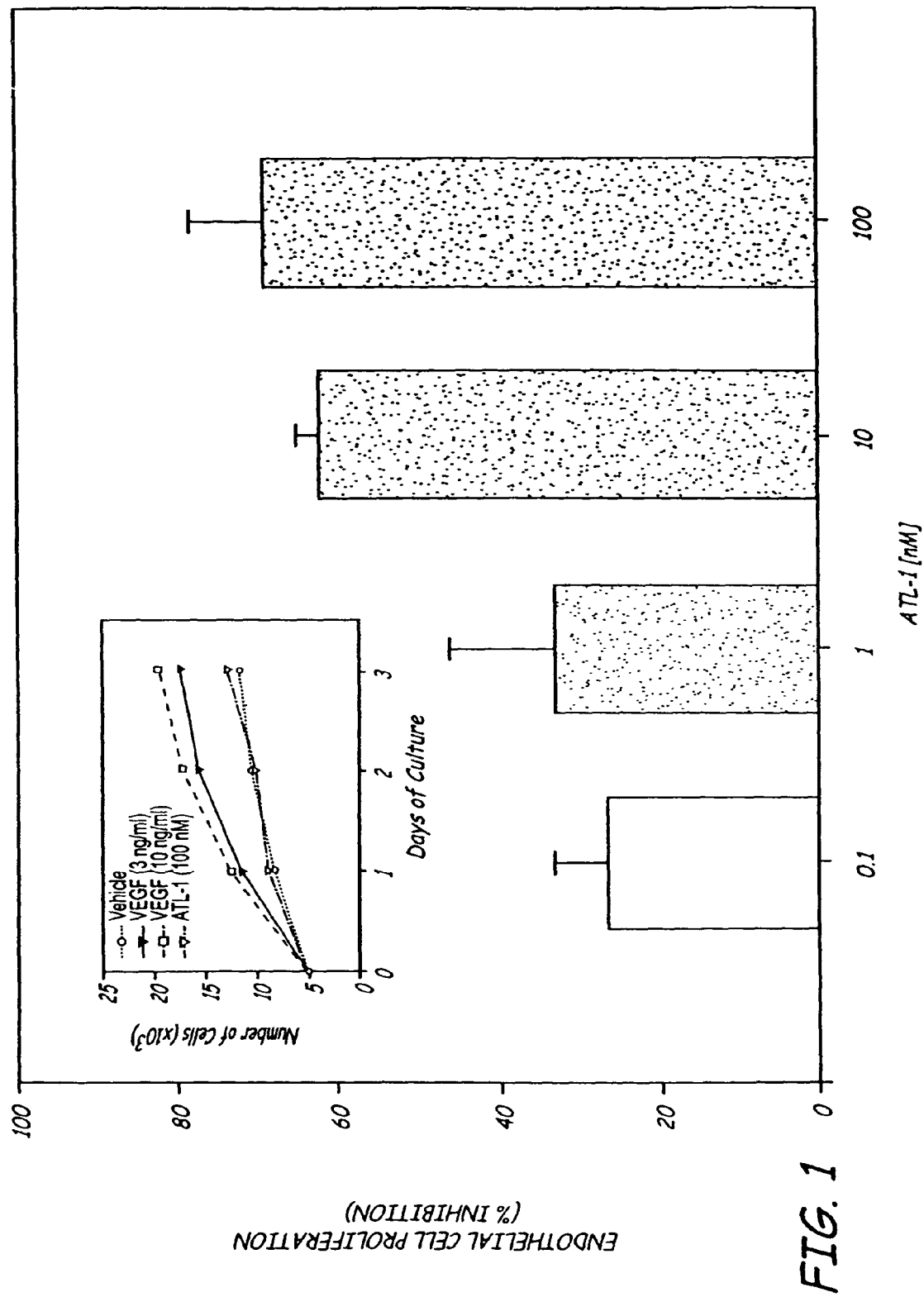
FIG. 1 demonstrates that ATL-1 inhibits VEGF-stimulated HUVEC proliferation. HUVEC ($5 \times 10^3$) were plated in 96-well culture plates and cell proliferation was stimulated with 3 ng/ml VEGF. Three days after treatment, cell numbers were measured using MTT assay. Results are expressed as percent inhibition of proliferation relative to vehicle and represent mean ±SE for four independent experiments performed in triplicate Inset: Representative experiment showing the time course of cell proliferation induced by 3 ng/ml (filled triangle) or 10 ng/ml (filled square) VEGF. Vehicle (open circles) and ATL-1 (100 nM) (open triangle).

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Abbreviations used throughout the present application include the following and are included here for convenience. ASA, aspirin; ATL, aspirin-triggered 15-epi-lipoxins; ATL-1, 15-epi-16-(para-fluoro)-phenoxy-lipoxin $A_4$; COX, cyclooxygenase; HETE, hydroxyeicosatetraenoic acid; HUVEC, human umbilical vein endothelial cells; IL, interleukin; LO, lipoxygenase; LT, leukotriene; LX, lipoxin; $LXA_4$, 5S,6R,15S-trihydroxy-7,9,13-trans-11-cis-eicosatetraenoic acid; 15-epi-$LXA_4$, 5S,6R,15R-trihydroxy-7,9,13-trans-11-cis-eicosatetraenoic acid; 15-R/S-methyl, $LXA_4$, 5S,6R,15R/S-trihydroxy-15-methyl-7,9,13-trans-11-cis-eicosatetraenoic acid, methyl ester; $LXB_4$, 5S,14R,15S-trihydroxy-6,8,12-trans-10-cis-eicosatetraenoic acid; MTT, 3-(4,5-dimethylthiazol-2-yl)-2,5-diphenyltetrazolium; PBS, phosphate buffered saline; PG, prostaglandin; PMN, neutrophils; VEGF, vascular endothelial growth factor.

It is to be understood, that throughout the present specification, reference is often made to the therapeutic compounds of the inventions as esters, for example, ATL-1 as a carboxylic ester, i.e., methyl ester. However, all pharmaceutically acceptable salts, esters, amides, and prodrugs, including the carboxylic acid, are considered within the scope of the invention for the $LXA_4$, ATL and $LXB_4$ compounds. For convenience, this terminology has been minimized throughout the description but should be considered as part of the invention. Additionally, it should be understood that the terms $LXA_4$, 15-epi-$LXA_4$ and 15-R/S-methyl, $LXA_4$ also include all pharmaceutically acceptable salts, esters, amides, prodrugs and carboxylic acids.

Additionally, the hydroxyl(s) of ATLs, $LXA_4$s, and $LXB_4$s can be protected by various protecting groups, such as those known in the art. An artisan skilled in the art can readily determine which protecting group(s) can be useful for the protection of the hydroxyl group(s). Standard methods are known in the art and are more fully described in literature. For example, suitable protecting groups can be selected by the skilled artisan and are described in Green and Wuts, "Protecting Groups in Organic Synthesis", John Wiley and Sons, 1991, the teachings of which are incorporated herein by reference. Preferred protecting groups include TMS or TIPPS groups, and preferably acetate or proprionate groups.

For example, one or more hydroxyl groups can be treated with a mild base, such as triethylamine in the presence of an acid chloride or silyl chloride to facilitate a reaction between the hydroxyl ion and the halide. Alternatively, an alkyl halide can be reacted with the hydroxyl ion (generated by a base such as lithium diisopropyl amide) to facilitate ether formation.

It should also be understood that not all hydroxyl groups need be protected. One, two or all three hydroxyl groups can be protected. This can be accomplished by the stoichiometric choice of reagents used to protect the hydroxyl groups. Methods known in the art can be used to separate the mono, di- or tri-protected hydroxy compounds, e.g., HPLC, LC, flash chromatography, gel permeation chromatography, crystallization, distillation, etc.

One advantage of protecting one or more hydroxyl groups of ATL, $LXA_4$, or $LXB_4$ compounds, e.g., via acetates, is the ability to delay the complete metabolic uptake of the compound(s). This is one means by which the compound(s) can remain active over a prolonged period of time as the subject's body slowly removes the protecting group from the hydroxyl under normal physiological conditions. Additionally, by protecting one or more of the hydroxyl groups of these compounds, hydrolysis of the protecting group allows the medication to enter the biochemical pathway of the subject prior to degradation of the parent, unprotected, compound.

Methods to prepare lipoxin analogs (ATLs, $LXA_4$s, or $LXB_4$s) are known in the art. For example, U.S. Pat. Nos. 4,576,758, 4,560,514, 5,079,261, 5,049,681, 5,441,951, 5,648,512, 5,650,435, 6,048,897, 6,100,296, 6,177,468 and 6,316,648 and Japanese Patent Nos. 3,227,922, 63,088,153, 62,198,677 and 1,228,994 describe approaches to prepare lipoxin analogs. Publications by K. C. Nicolaou et al. include approaches to various lipoxin compounds. (For example see, Nicolaou, K. C. et al. Biochim. Biophys. Acta 1003:44-53; Nicolaou, K. C. et al. J. Org. Chem. 54:5527-5535; and Nicolaou, K. C. Angew. Chem. Int. Ed. Engl. 30:1100-1116. Additional literature references for the preparation of lipoxin analogs include Takano, T., S. Fiore, J. F. Maddox, H. R. Brady, N. A. Petasis, and C. N. Serhan. 1997. Aspirin-triggered 15-epi-lipoxin $A_4$ and $LXA_4$ stable analogs are potent inhibitors of acute inflammation: Evidence for anti-inflammatory receptors. J. Exp. Med. 185:1693-1704 and Serhan, Charles N., Maddox, Jane F., Petasis, Nicos A., Akritopoulou-Zanze, Irini, Papayianni, Aikaterina, Brady, Hugh R., Colgan, Sean P., and Madara, James L. (1995), Biochemistry, 34, pp. 14609-14614.

Aspirin's therapeutic mechanism of action includes inhibition of COX-derived prostanoids (10). It was discovered that COX-2, when acetylated by ASA, blocks the ability of COX-2 to generate prostanoids, yet this enzyme remains active in endothelial cells, epithelial cells and mononuclear cells and initiates the biosynthesis of new products of cell-cell interactions or transcellular biosynthesis termed aspirin-triggered-15-epi-lipoxins (ATLs) (11). These novel endogenous lipid mediators are the carbon 15 epimers of LX that carry their 15 alcohol in the R configuration compared to their native lipoxin (LX) counterparts and appear to mimic most if not all endogenous LX bioactivities.

To date the actions of ATLs appear to be most relevant in regulating inflammatory responses, since they are generated during cell-cell interactions that can involve, for example, endothelial cells-neutrophils in vivo (12), and display potent inhibitory actions in several key and strategic events in inflammation (12-14). Both LX and ATL actions include inhibiting adhesion and transmigration of neutrophils, and hence can serve as counterregulatory signals to limit and/or regulate leukocyte accumulation that are potentially operative in the dampening and resolution of inflammatory sites (14). Since LX are rapidly generated and inactivated in the local microenvironment, to investigate these actions in vivo, stable analogs of both lipoxins, i.e., $LXA_4$ and ATL were designed that enhance bioavailabilities and these natural compounds bioactivities compared to their native products (14) and also proved to be ~100 times the potency of ASA (13). The present invention establishes that $LXA_4$s and ATLs can regulate angiogenesis, a previously unknown and surprising application of these compounds. For example, using a metabolically more stable ATL synthetic analog [15-epi-16-(para-fluoro)-phenoxy-lipoxin $A_4$ (denoted ATL-1)], ATLs and $LXA_4$ compounds, including, 15-epi-$LXA_4$ or 15-R/S-methyl, $LXA_4$ and $LXA_4$ proved to be potent angiostatic eicosanoid in vivo, identifying a new activity for these endogenous mediators that is in sharp contrast to the actions of other eicosanoids and is relevant in several human diseases.

In one aspect, the present invention pertains to methods for the prevention, diminishment or inhibition of angiogenesis. The method is accomplished by the administration of an effective amount of $LXA_4$ and analogs thereof, such as 15-R/S methyl, $LXA_4$, and pharmaceutically acceptable salts, esters, amides or prodrugs thereof, to a subject in need thereof. As a consequence of the action of the therapeutic agent, angiogenesis is prevented, reduced or inhibited in the subject. More specifically, the therapeutic agents can be used in the treatment of the disease states and conditions of the angiogenic disease processes as described below. More specifically, the $LXA_4$ and ATL therapeutic compounds described throughout the specification can be used for the treatment of restenosis, solid tumor tissue growth, neovascularization, e.g., retinal tissue, and reducing blood supply to tissue required to support new growth of tissue in a subject.

In another aspect, the present invention also pertains to methods for the prevention, reduction or inhibition of angiogenesis in tissue of a subject. The method is accomplished by the administration of an effective amount of an aspirin triggered lipoxin (ATL) (15-epi-$LXA_4$, such as 15-epi-16-(para-fluoro)-phenoxy-lipoxin $A_4$ (ATL-1)), and pharmaceutically acceptable salts, esters, amides or prodrugs thereof, to a subject in need thereof. As a consequence of the action of the therapeutic agent, angiogenesis is prevented or inhibited in the subject.

The invention thus provides for a method for the general inhibition of angiogenesis in tissue, and thereby inhibits or prevent events in the tissue which depend upon angiogenesis. Generally, the method comprises administering to the tissue a composition comprising an angiogenesis-inhibiting amount of, for example, ATL-1, $LXA_4$, 15-epi-$LXA_4$ or 15-R/S-methyl, $LXA_4$.

As used herein, the term "angiogenesis" means the formation of new blood vessels into a tissue or organ. Under normal physiological conditions, humans or animals only undergo angiogenesis in very specific restricted situations. For example, angiogenesis is associated with wound healing, fetal and embryonal development and formation of the corpus luteum, endometrium and placenta. The biochemical aspects of angiogenesis are associated with a highly regulated system of angiogenic stimulators and inhibitors. Controlled angiogenesis has been found to be altered in certain disease states and, in many cases, the pathological damage associated with the disease is related to the uncontrolled angiogenesis.

The bioprocesses of controlled and uncontrolled angiogenesis are thought to occur in a similar manner. Endothelial cells and pericytes, surrounded by a basement membrane, form capillary blood vessels. Erosion of the basement membrane promotes angiogenesis by enzymes released by endothelial cells and leukocytes. The endothelial cells, which line the lumen of blood vessels, then break through the basement membrane. Angiogenic stimulants induce the endothelial cells to migrate through the eroded basement membrane. The migrating cells form an offshoot from the parent blood vessel, where the endothelial cells undergo mitosis and proliferate. The endothelial offshoots can merge with each other to form capillary loops, creating a new blood vessel. In the disease state, prevention of angiogenesis could avert the damage caused by the invasion of the new microvascular system.

Persistent, unregulated angiogenesis can occur in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. The present invention provides therapies that are directed to control the angiogenic processes thus leading to the abrogation or mitigation of these diseases. With the exception of traumatic wound healing, corpus leuteum formation and embryogenesis, it is believed that angiogenesis processes are associated with undesired, and often life threatening, disease processes and therefore, the use of the present therapeutic methods are selective for the disease, i.e., angiogenesis, and do not have deleterious side effects.

The following angiogenic diseases can be treated according to the present invention by use of the afore-mentioned ATLs, such as ATL-1 or $LXA_4$s such as 15-R/S-methyl, $LXA_4$. These angiogenic diseases include, but are not limited to, the following:

One example of a disease mediated by angiogenesis is ocular neovascular disease. This disease is characterized by invasion of new blood vessels into the structures of the eye such as the retina or cornea. It is perhaps, one of the most common causes of blindness and is involved in over twenty eye diseases. For example, in age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, Vitamin A deficiency, contact lens overwear, atopic keratitis, superior limbic keratitis, epidemic keratoconjunctivitis, pterygium keratitis sicca, sjogrens, acne rosacea, lipid degeneration, chemical burns, bacterial ulcers, fungal ulcers, phylectenulosis, syphilis, Mycobacteria infections, Herpes simplex infections, Herpes zoster infections, Wegeners sarcoidosis, Scleritis, Steven's Johnson syndrome, periphigoid radial keratotomy, protozoan infections, Kaposi sarcoma, Mooren ulcer, Terrien's marginal degeneration, marginal keratolysis, rheumatoid arthritis, systemic lupus, polyarteritis, trauma, and corneal graph rejection.

Diseases associated with retinal/choroidal neovascularization include, but are not limited to, diabetic retinopathy, vein occlusion, artery occlusion, carotid obstructive disease, chronic uveitis/vitritis, mycobacterial infections, Lyme's disease, systemic lupus erythematosis, macular degeneration, sickle cell anemia, sarcoid, syphilis, pseudoxanthoma elasticum, Pagets disease, retinopathy of prematurity, Eales disease, Bests disease, myopia, optic pits, Stargarts disease, pars planitis, chronic retinal detachment, hyperviscosity syndromes, toxoplasmosis, Bechets disease, infections causing a retinitis or choroiditis, presumed ocular histoplasmosis, trauma and post-laser complications. Other diseases include, but are not limited to, diseases associated with rubeosis and diseases caused by the abnormal proliferation of fibrovascular or fibrous tissue including all forms of proliferative vitreoretinopathy.

An even more prevalent disease in which angiogenesis is believed to be involved is rheumatoid arthritis. For example, the blood vessels in the synovial lining of the joints undergo angiogenesis. In addition to forming new vascular networks, the endothelial cells release factors and reactive oxygen species that lead to pannus growth and cartilage destruction. It is believed that the factors involved in angiogenesis can actively contribute to, and help maintain, the chronically inflamed state of rheumatoid arthritis.

It is believed that factors associated with angiogenesis can also have a role in osteoarthritis. The activation of the chondrocytes by angiogenic-related factors contributes to the destruction of the joint. At a later stage, the angiogenic factors can promote new bone formation. The present invention provides therapeutic intervention that prevents the bone destruction and can halt the progress of the disease and provide relief for persons suffering with arthritis.

Both ulcerative colitis and Crohn's disease are known to have histological changes with the ingrowth of new blood vessels into the inflamed tissues. Bartonellosis, can result in a chronic stage that is characterized by proliferation of vascular endothelial cells. An even more insidious pathological role associated with angiogenesis is found in arteriosclerosis. The plaquing of the lumen of blood vessels has been shown to have angiogenic stimulatory activity.

A frequent angiogenic disease of childhood is hemangioma. Generally, the tumors associated with the disease are benign and regress without intervention. In more severe cases, the tumors grow and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. These diseases are characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Of great concern is the disease state(s) associated with cancer(s). Often times, the cancer is associated with angiogenesis and is identified by solid tumor formation and metastasis. Angiogenic factors are associated with several solid tumors such as neuroblastoma, rhabdomyosarcomas, retinoblastoma, Ewing sarcoma, and osteosarcoma. It is known that a tumor cannot expand without a blood supply to provide nutrients and remove cellular wastes. Tumors in which angiogenesis is important include solid tumors, and benign tumors such as acoustic neuroma, neurofibroma, trachoma and granulomas. Prevention or inhibition of angiogenesis could prevent or halt the growth of these tumors and the subsequent degenerative condition due to the presence of the tumor.

Angiogenesis has also been associated with blood-born tumors including leukemias, any of the various acute or chronic neoplastic diseases of bone marrow in which unrestrained proliferation of white blood cells occurs, usually accompanied by anemia, impaired blood clotting, and enlargement of the lymph nodes, liver, and spleen. It is believed that angiogenesis is significant as a caustive factor in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. Once the tumor cells leave the primary site, and find a secondary metastasis site, angiogenesis must occur before the new tumor can grow and expand. Therefore, prevention of angiogenesis could prevent metastasis of tumors and contain the neoplastic growth at the primary site.

In a related embodiment, the present invention can be used in combination with other therapies such as conventional chemotherapy directed against solid tumors and metastases. ATLs, such as ATL-1 or $LXA_4$s, such as 15-R/S-methyl, $LXA_4$, can be administered during or after chemotherapy. In a preferred embodiment, the drug should be administered when the tumor tissue is responding to the toxic assault when vascular tissue is being reorganized to supply blood and nutrients to the tumor tissue. Additionally, the use of ATLs, such as ATL-1 or $LXA_4$s can be used as a phrophylatic treatment after surgical removal of a tumor to prevent angiogenesis from occurring at the treatment site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and can be caused or exacerbated by angiogenesis. Adhesions are a frequent complication of surgery and lead to problems such as small bowel obstruction.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition, reduction or prevention of restenosis by inhibiting, reducing or preventing angiogenesis according to the present methods in a subject following angioplasty procedures. For inhibition or prevention of restenosis, an ATL, such as ATL-1 or an $LXA_4$, such as 15-R/S-methyl, $LXA_4$, can be administered, preferably via intravenous injection, several days before the operation or after the angioplasty procedure for from about 2 to about 28 days, and more typically for about the first 14 days following the procedure.

The term "subject" as used herein refers to any living organism in which an angiogenic response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "mammal" as used herein refers to a living organism capable of eliciting an immune response to an antigen. The term subject includes, but is not limited to, nonhuman primates such as chimpanzees and other apes and monkey species, sheep, pigs, goats, horses, dogs, cats, mice, rats and guinea pigs, and the like.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These can include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is identified, those of skill in the pharmaceutical art generally can design prodrugs of the compound [see, e.g., Nogrady (1985) Medicinal Chemistry A Biochemical Approach, Oxford University Press, New York, pages 388-392]. Conventional procedures for the selection and preparation of suitable prodrug derivatives are described, for example, in "Design of Prodrugs," ed. H. Bundgaard, Elsevier, 1985. Suitable examples of prodrugs include methyl, ethyl and glycerol esters of the corresponding acid.

The compounds of the invention can be formulated into pharmaceutical compositions as described, vide infra. In a preferred embodiment, the compound can be administered over an extended period of time in a sustained release composition. Sustained release compositions are known in the art and one skilled in the art can formulate an acceptable composition based on generally recognized parameters in the art. In a most preferred embodiment, the glycerol ester can be used in the treatment of inflammatory conditions, described herein, in sustained release compositions, i.e., a transdermal patch, as known in the art. Suitable methods to prepare a transdermal patch can be found in U.S. Pat. No. 5,814,599, 5,846,974 or 4,201,211, the contents of which are incorporated herein by reference. More particularly, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with the inflammatory condition.

A "therapeutically effective amount" is an amount of an ATL, such as ATL-1 or an LXA$_4$, such as 15-R/S-methyl, LXA$_4$, sufficient to produce a measurable inhibition, reduction or prevents angiogenesis in the tissue being treated, i.e., an angiogenesis-inhibiting amount. Inhibition of angiogenesis can be measured in situ by immunohistochemistry or by other methods known to one skilled in the art such as measurement by FAC analysis that monitors P-selectin or VEGF receptors. See also FIGS. 4 and 5.

More specifically, the pharmaceutical compositions of the invention can include a "therapeutically effective amount" or a "prophylactically effective amount" of an antiangiogenic of the invention. A "therapeutically effective amount" refers to an amount effective, at dosages and for periods of time necessary, to achieve the desired therapeutic result, e.g., a diminishment, reduction or prevention of angiogenic factors associated with various disease states or conditions. A therapeutically effective amount of the antiangiogenic can vary according to factors such as the disease state, age, sex, and weight of the individual, and the ability of the antiangiogenic to elicit a desired response in the individual. A therapeutically effective amount is also one in which any toxic or detrimental effects of the antibody or antibody portion are outweighed by the therapeutically beneficial effects.

A "prophylactically effective amount" refers to an amount effective, at dosages and for periods of time necessary, to achieve the desired prophylactic result, i.e. prevent. Typically, since a prophylactic dose is used in subjects prior to or at an earlier stage of disease, the prophylactically effective amount will be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antiangiogenic of the invention is 0.1-20 mg/kg, more preferably 1-10 mg/kg. It is to be noted that dosage values can vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The antiangiogenic compounds of the invention, e.g., an ATL, such as ATL-1 or an $LXA_4$, such as 15-R/S-methyl, $LXA_4$, can be incorporated into pharmaceutical compositions suitable for administration to a subject. Typically, the pharmaceutical composition comprises an antiangiogenic of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In some instances, it can be beneficial to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the antiangiogenic.

Additionally, the mono-, di- and/or tri-protected alcohols of the compounds of the invention provide for sustained release of the inhibitory/preventative compound. For example, the tri-acyl analogs of the invention provide for such a sustained release of the hydrolyzed tri-hydroxy alcohol(s). The triacylated analogs are thus de-esterified in the blood of the subject.

The antiangiogenics of the invention can be incorporated into a pharmaceutical composition suitable for parenteral administration. Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention can be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antiangiogenic is administered by intravenous infusion or injection. In another preferred embodiment, the antiangiogenic is administered by intramuscular or subcutaneous injection. In the most preferred embodiment, the antiangiogenic is administered orally.

Alternatively, a preferred embodiment includes the use of the compounds of the invention in eye-drop solutions. This provides for application to the ease to inhibit or prevent ocular diseases such as glaucoma. Generally, the active ingredient, i.e., the compounds of the invention, would be dissolved in an aqueous solution that can be applied directly to the eye.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antiangiogenics of the present invention can be administered by a variety of methods known in the art. As will be appreciated by the skilled artisan, the route and/or mode of administration will vary depending upon the desired results. In certain embodiments, the active compound can be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antiangiogenic of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the compounds can be incorporated with excipients and used in the form of ingestible tablets, buccal tablets, troches, capsules, elixirs, suspensions, syrups, wafers, and the like. To administer a compound of the invention by other than parenteral administration, it can be necessary to coat the compound with, or co-administer the compound with, a material to prevent its inactivation.

The present invention also provides for packaged pharmaceutical compositions useful in the prevention or inhibition of angiogenic activity in a subject. The packaged pharmaceutical composition includes a container holding a therapeutically effective amount of at least one ATL, such as ATL-1 or an $LXA_4$, such as 15-R/S-methyl, $LXA_4$, or a pharmaceutically acceptable salt, esters, amide, or prodrug thereof and instructions for using the therapeutic compound for preventing, reducing or inhibiting angiogenic activity in the subject. Additionally, the present invention provides therapeutically effective amounts of packaged pharmaceutical compositions, e.g., ATL-1, $LXA_4$, 15-epi-$LXA_4$ or 15-R/S-methyl, $LXA_4$ or pharmaceutically acceptable salts, esters, amides, and prodrugs thereof, and instructions useful to treat, i.e., inhibit or prevent, solid tumor tissue growth from undergoing neovascularization, neovascularization from occurring, neovascularization from occurring in retinal tissue, restenosis from occurring following angioplasty in a tissue wherein smooth muscle cell migration occurs, or reducing blood supply to a tissue required to support new growth of new angiogenic tissue.

The present invention also provides angeogenic compounds that facilitate angiogenesis. Surprisingly, configurational isomers of $LXA_4$, $LXA_4$ analogs and ATL analogs, $LXB_4$ and $LXB_4$ analogs and pharmaceutically acceptable salts, esters, amides or prodrugs thereof, provide the opposite effects with regard to revascularization of tissue by the above-identified compounds of the invention. That is, it has been surprisingly discovered that $LXB_4$ and $LXB_4$ analogs have the ability to stimulate regeneration and ingrowth of vascular or epithelial tissue in tissues that are in need of such stimulation. This is especially important in tissue grafting, tissue engineering and prosthetic group sites of attachment. Therefore, the present invention provides methods of tissue regeneration, compounds for such application and packaged pharmaceuticals to accomplish such results.

For example, cardiovascular disease occurs as a consequence of the partial or complete blockage of vessels carrying blood in the coronary vascular system and in peripheral vasculature. Occlusion of the vessel can results in death of tissue previously nourished by the occluded vessels or inability of the vessels to transport sufficient blood supply to regions requiring high blood consumption and accompanying nutrients. Blood vessel occlusion can be partially compensated by the natural process of angiogenesis, in which new conduits are formed to replace the function of the impaired vessels. These new conduits are referred to as "collateral" vessels and can help in the restoration of blood flow to the deprived tissue, thereby constituting natural bypasses around the occluded vessels. However, some individuals for various reasons are unable to generate sufficient collateral vessels to manage the consequences of diminished blood flow from cardiovascular disease.

The $LXB_4$ compounds of the invention can be used to enhance the body's natural ability to repair itself by undergoing natural angiogenesis. As can be seen from the contents of the specification and Figures, vessel growth is stimulated by these unique compounds. This process and use of the present compounds can be utilized for the treatment of wounds. The $LXB_4$ compounds help stimulate the healing process, causing re-epithelialization and vascularization to occur.

Suitable lipoxin analogs, including ATLs, $LXA_4$s and $LXB_4$s encompassed by the present invention include those having the following characteristics.

The instant lipoxins comprising an "active region" and a "metabolic transformation region" as both terms are defined herein are generally of the following structure:

wherein $R_1$ can be

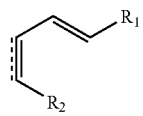

wherein $R_1$ can be

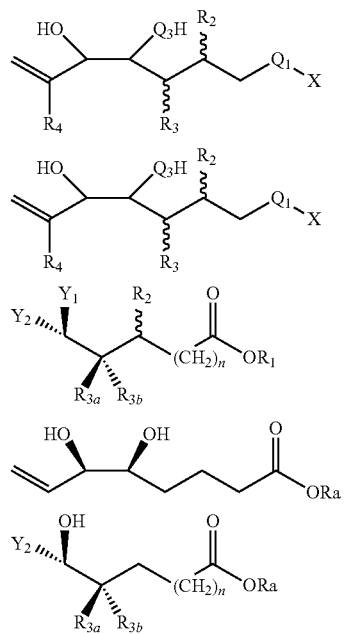

and $R_2$ can be

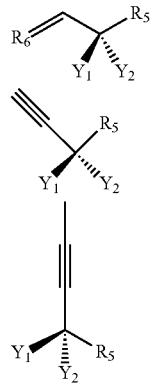

-continued

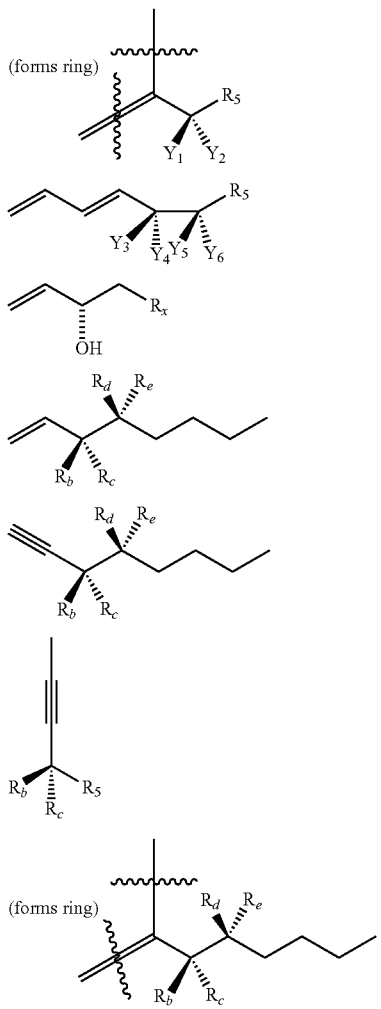

In one embodiment, the lipoxin analogs of this invention have the following structural formula I:

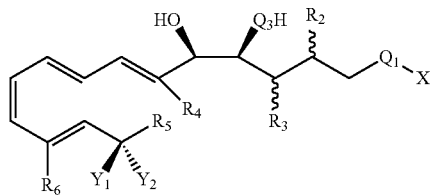

wherein X is $R_1$, $OR_1$, or $SR_1$;

wherein $R_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) phenyl;

(vi) substituted phenyl wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which can be a straight chain or branched, and hydroxyl;

(vii) a detectable label molecule; or (viii) a straight or branched chain alkenyl of 2 to 8 carbon atoms, inclusive; wherein $Q_1$ is $(C=O)$, $SO_2$ or $(CN)$;

wherein $Q_3$ is O, S or NH;

wherein one of $R_2$ and $R_3$ is a hydrogen atom and the other is (a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is $-O-$ or $-S-$;

wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;

wherein $R_4$ is (a) a hydrogen atom;

(b) an alkyl of 1 to 6 carbon atoms, inclusive, which can be straight chain or branched;

wherein $Y_1$ or $Y_2$ is $-OH$, methyl, or $-SH$ and wherein the other is (a) a hydrogen atom (b) $CH_aZ_b$ where a+b=3, a=0 to 3, b=0 to 3; and each Z, independently, is a cyano, a nitro, or a halogen atom;

(c) an alkyl of 2 to 4 carbon atoms, inclusive, straight chain or branched; or (d) an alkoxy of 1 to 4 carbon atoms, inclusive;

or $Y_1$ and $Y_2$ taken together are (a) $=NH$; or (b) $=O$;

wherein $R_5$ is (a) an alkyl of 1 to 9 carbon atoms which can be straight chain or branched;

(b) $-(CH_2)_n-R_i$ wherein n=0 to 4 and $R_i$ is (i) a cycloalkyl of 3 to 10 carbon atoms, inclusive;

(ii) a phenyl; or (iii) substituted phenyl

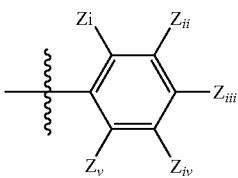

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) $R_a Q_a R_b$
wherein $Q_a$ is O or S;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
(d) —C($R_{iii}$)($R_{iv}$)—$R_i$
wherein $R_{iii}$ and $R_{iv}$ are each, independently:
(i) a hydrogen atom;
(ii) $CH_a Z_b$ where a+b=3, a=0 to 3, b=0+3, and wherein each Z, independently, is a cyano, a nitro, or a halogen atom;
(e) a haloalkyl of 1 to 8 carbon atoms, inclusive, and 1 to 6 halogen atoms, inclusive, straight chain or branched; and
wherein $R_6$ is
(a) a hydrogen atom;
(b) an alkyl from 1 to 4 carbon atoms, inclusive, straight chain or branched;
(c) a halogen.
In one embodiment of this invention, the lipoxin analogs have the following structure II:

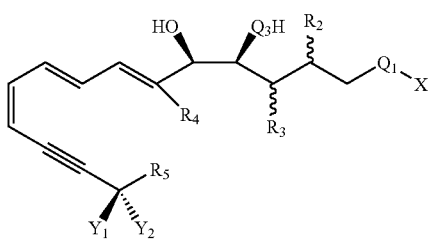

wherein X is $R_1$, $OR_1$, or $SR_1$; wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) a phenyl;
(vi) substituted phenyl

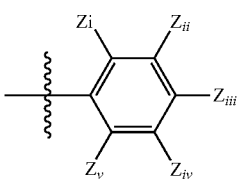

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(vii) a detectable label molecule, such as but not limited to fluorescent labels; or
(viii) an alkenyl of 2 to 8 carbon atoms, inclusive, straight chain or branched;
wherein $Q_1$ is (C=O), $SO_2$ or (C=N);
wherein $Q_3$ is O, S or NH;
wherein one of $R_2$ and $R_3$ is hydrogen and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_a Q_2 R_b$
wherein $Q_2$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
wherein $R_4$ is
(a) a hydrogen atom;
(b) alkyl of 1 to 6 carbon atoms, inclusive, which can be straight chain or branched;
wherein $Y_1$ or $Y_2$ is —OH, methyl, —H or —SH and wherein the other is
(a) a hydrogen atom;
(b) $CH_a Z_b$
where a+b=3, a=0 to 3, b=0 to 3
wherein each Z, independently, is a cyano, a nitro, or a halogen atom;
(c) an alkyl of 2 to 4 carbon atoms, inclusive, straight chain or branched;
(d) an alkoxy of 1 to 4 carbon atoms, inclusive; or $Y_1$ and $Y_2$ taken together are
(a) =NH; or
(b) =O;
wherein $R_5$ is
(a) an alkyl of 1 to 9 carbon atoms which can be straight chain or branched;
(b) —$(CH_2)_n$—$R_i$
wherein n=0 to 4 and $R_i$ is
(i) a cycloalkyl of 3 to 10 carbon atoms, inclusive;
(ii) phenyl; or
(iii) substituted phenyl

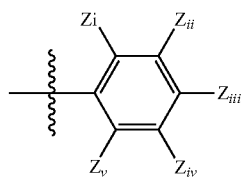

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) —$R_a Q_a R_b$
wherein $Q_a$ is —O— or —S—; and
wherein $R_a$ is alkylene of 0 to 6 carbons atoms, inclusive, which can be straight chain or branched;

wherein $R_b$ is alkyl of 0 to 8 carbon atoms, inclusive, which can be straight chain or branched;

(d) —C($R_{iii}$)($R_{iv}$)—$R_i$ wherein $R_{iii}$ and $R_{iv}$ are each independently:

(i) a hydrogen atom; or (ii) $CH_aZ_b$ where a+b=3, a=0 to 3, b=0+3 wherein each Z, independently, is a cyano, a nitro, or a halogen atom, (e) a haloalkyl of 1 to 8 carbon atoms, inclusive, and 1 to 6 halogen atoms, inclusive, straight chain or branched.

In one embodiment of this invention, the lipoxin analogs have the following structure III:

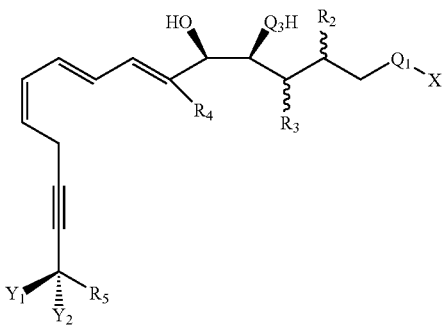

wherein X is $R_1$, $OR_1$, or $SR_1$; wherein $R_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) phenyl;

(vi) substituted phenyl

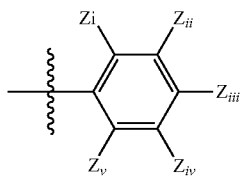

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(vii) a detectable label molecule; or (viii) an alkenyl of 2 to 8 carbon atoms, inclusive, straight chain or branched;

wherein $Q_1$ is (C=O), $SO_2$ or (C=N);

wherein $Q_3$ is O, S or NH;

wherein one of $R_2$ and $R_3$ is hydrogen atom and the other is (a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is —O— or —S—;

wherein $R_a$ is alkylene of 0 to 6 carbons atoms, inclusive, which can be straight chain or branched;

wherein $R_b$ is alkyl of 0 to 8 carbon atoms, inclusive, which can be straight chain or branched;

wherein $R_4$ is (a) a hydrogen atom; or (b) an alkyl of 1 to 6 carbon atoms, inclusive, which can be straight chain or branched;

wherein $Y_1$ or $Y_2$ is hydroxyl, methyl, hydrogen or thiol and wherein the other is (a) a hydrogen atom;

(b) $CH_aZ_b$ where a+b=3, a 0 to 3, b=0 to 3 wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive; or $Y_1$ and $Y_2$ taken together are (a) =NH; or (b) =O; and wherein $R_5$ is (a) an alkyl of 1 to 9 carbon atoms, which can be straight chain or branched;

(b) —$(CH_2)_n$—$R_i$ wherein n=0 to 4 and $R_i$ is (i) cycloalkyl of 3 to 10 carbon atoms, inclusive;

(ii) phenyl;

(iii) substituted phenyl

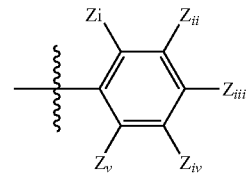

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) $R_aQ_aR_b$ wherein $Q_a$ is —O— or —S—;

wherein $R_a$ is alkylene of 0 to 6 carbons atoms, inclusive, which can be straight chain or branched;

wherein $R_b$ is alkyl of 0 to 8 carbon atoms, inclusive, which can be straight chain or branched; or (d) —C($R_{iii}$)($R_{iv}$)—$R_i$ wherein $R_{iii}$ and $R_{iv}$ are each independently:

(i) a hydrogen atom; or (ii) $CH_aZ_b$ where a+b=3, a=0 to 3, b=0+3 wherein each Z, independently, is a cyano, a nitro, or a halogen atom, (e) a haloalkyl of 1 to 8 carbon atoms, inclusive, and 1 to 6 halogen atoms, inclusive, straight chain or branched.

In another embodiment of this invention, lipoxin analogs have the following structural formula IV:

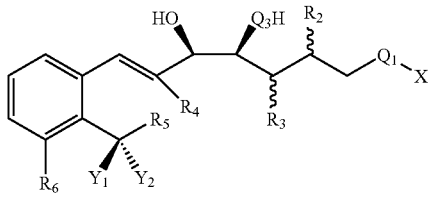

wherein X is $R_1$, $OR_1$, or $SR_1$; wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

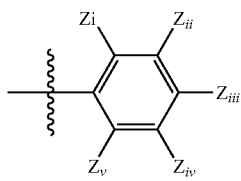

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which can be a straight chain or branched, and hydroxyl;
(vii) a detectable label molecule; or
(viii) an alkenyl of 2 to 8 carbon atoms, inclusive, straight chain or branched;
wherein $Q_1$ is (C=O), $SO_2$ or (CN);
wherein $Q_3$ is O, S or NH;
wherein one of $R_2$ and $R_3$ is hydrogen and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_a Q_2 R_b$
wherein $Q_2$ is $-O-$ or $-S-$;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
wherein $R_4$ is
(a) a hydrogen atom; or
(b) an alkyl of 1 to 6 carbon atoms, inclusive, which can be straight chain or branched;
wherein $Y_1$ or $Y_2$ is $-OH$, methyl, or $-SH$ and wherein the other is
(a) a hydrogen atom;
(b) $CH_3Z_b$ where a+b=3, a=0 to 3, b=0 to 3, wherein each Z, independently, is a cyano, a nitro, or a halogen atom;
(c) an alkyl of 2 to 4 carbon atoms, inclusive, straight chain or branched; or
(d) an alkoxy of 1 to 4 carbon atoms, inclusive;
or $Y_1$ and $Y_2$ taken together are (a) =NH; or
(b) =O;
wherein $R_5$ is
(a) an alkyl of 1 to 9 carbon atoms which can be straight chain or branched;
(b) $-(CH_2)_n-R_i$
wherein n=0 to 4 and $R_i$ is
(i) a cycloalkyl of 3 to 10 carbon atoms, inclusive;
(ii) phenyl; or
(iii) substituted phenyl

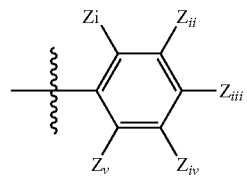

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which can be a straight chain or branched, and hydroxyl;
(c) $R_a Q_a R_b$
wherein $Q_a$ is $-O-$ or $-S-$;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
(d) $-C(R_{iii})(R_{iv})-R_i$
wherein $R_{iii}$ and $R_{iv}$, are each independently:
(i) a hydrogen atom; or
(ii) $CH_aZ_b$ where a+b=3, a=0 to 3, b=0+3 and
wherein each Z, independently, is a cyano, a nitro, or a halogen atom; or
(e) haloalkyl of 1 to 8 carbon atoms, inclusive, and 1 to 6 halogen atoms, inclusive, straight chain or branched; and
wherein $R_6$ is
(a) a hydrogen atom;
(b) an alkyl from 1 to 4 carbon atoms, inclusive, straight chain or branched; or
(c) a halogen atom.
In another embodiment of this invention, lipoxin analogs have the following structural formula V:

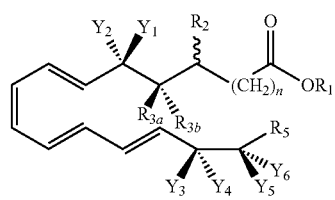

wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

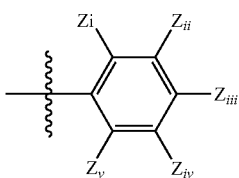

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(vii) a detectable label molecule; or (viii) an alkenyl of 2 to 8 carbon atoms, inclusive, straight chain or branched;

wherein n=1 to 10, inclusive;

wherein $R_2$, $R_{3a}$, and $R_{3b}$ are each independently:

(a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is —O— or —S—;

wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;

wherein $Y_1$ or $Y_2$ is —OH, methyl, hydrogen, or —SH and wherein the other is (a) a hydrogen atom;

(b) $CH_aZ_b$ where a+b=3, a=0 to 3, b=0 to 3, and wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or $Y_1$ and $Y_2$ taken together are (a) =NH; or (b) =O;

wherein $Y_3$ or $Y_4$ is —OH, methyl, hydrogen, or —SH and wherein the other is (a) a hydrogen atom;

(b) $CH_aZ_b$ wherein a+b=3, a=0 to 3, b=0 to 3, and wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or $Y_3$ and $Y_4$ taken together are (a) =NH; or (b) =O;

wherein $Y_5$ or $Y_6$ is —OH, methyl, hydrogen, or —SH and wherein the other is (a) a hydrogen atom;

(b) $CH_aZ_b$ where a+b=3, a=0 to 3, b=0 to 3 wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or $Y_5$ and $Y_6$ taken together are (a) =NH; or (b) =O;

wherein $R_5$ is (a) an alkyl of 1 to 9 carbon atoms which can be straight chain or branched;

(b) —$(CH_2)_n$—$R_i$ wherein n=0 to 4 and $R_i$ is (i) a cycloalkyl of 3 to 10 carbon atoms, inclusive;

(ii) phenyl; or (iii) substituted phenyl

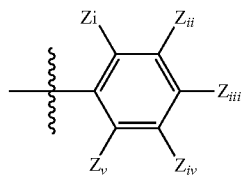

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) —$R_aQ_aR_b$ wherein $Q_a$ is —O— or —S—; and wherein $R_a$ is alkylene of 0 to 6 carbons atoms, inclusive, which can be straight chain or branched;

wherein $R_b$ is either alkyl of 0 to 8 carbon atoms, inclusive, which can be straight chain or branched or substituted phenyl;

(d) —C($R_{iii}$)($R_{iv}$)—$R_i$ wherein $R_{iii}$ and $R_{iv}$ are each independently:

(i) a hydrogen atom; or (ii) $CH_aZ_b$ where a+b=3, a=0 to 3, b=0+3, and wherein each Z, independently, is a cyano, a nitro, or a halogen atom; or (e) haloalkyl of 1 to 8 carbon atoms, inclusive, and 1 to 6 halogen atoms, inclusive, straight chain or branched.

In another embodiment of this invention, lipoxin analogs have the structural formula VI:

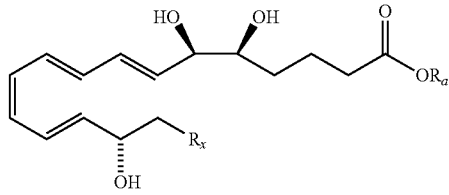

wherein $R_a$ is (a) a hydrogen atom; or (b) alkyl of 1 to 8 carbon atoms;

wherein $R_x$ is (a) substituted phenyl

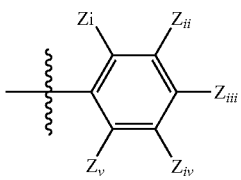

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(b) a substituted phenoxy

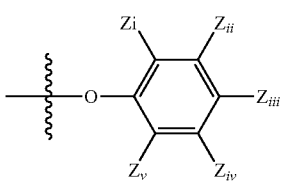

wherein $Z_i$ through $Z_v$ are as defined above; or

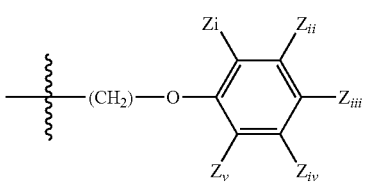

wherein $Z_i$ through $Z_v$ are as defined above.

In another preferred embodiment of this invention, lipoxin analogs have the following structural formula VII:

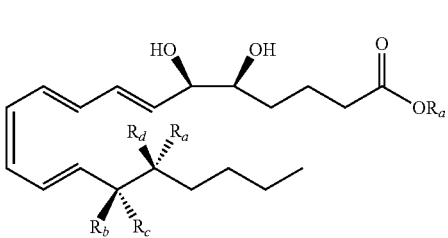

wherein $R_a$ is
(a) a hydrogen atom; or
(b) an alkyl of 1 to 8 carbon atoms;
wherein $R_b$ and $R_c$ are each independently:
(a) a hydrogen atom;
(b) a hydroxyl, or a thiol;
(c) a methyl or a halomethyl;
(d) a halogen;
(e) an alkoxy of 1 to 3 carbon atoms;
wherein $R_d$ and $R_e$ are each independently:
(a) a hydrogen atom;
(b) a hydroxyl, or thiol;
(c) a methyl or halomethyl;
(d) a halogen;
(e) an alkoxy of 1 to 3 carbon atoms; or
(f) an alkyls or haloalkyl of 2 to 4 carbon atoms, inclusive, which can be straight chain or branched.

In another preferred embodiment of this invention, the lipoxin analogs have the structural formula VIII:

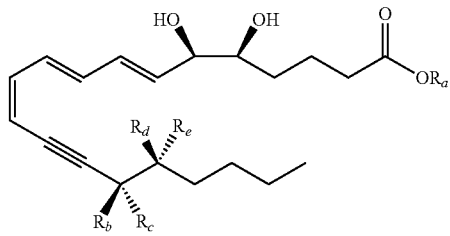

wherein $R_a$ is
(a) a hydrogen atom; or
(b) an alkyl of 1 to 8 carbon atoms;
wherein $R_b$ and $R_c$ are each independently:
(a) a hydrogen atom;
(b) a hydroxyl or a thiol;
(c) a halomethyl;
(d) a halogen;
(e) an alkyl of 1 to 3 carbon atoms, inclusive, straight chain or branched; or
(f) an alkoxy of 1 to 3 carbon atoms, inclusive;
wherein $R_d$ and $R_e$ are each independently:
(a) a hydrogen atom;
(b) a hydroxyl, or a thiol;
(c) a methyl or a halomethyl;
(d) a halogen;
(e) an alkoxy of 1 to 3 carbon atoms, inclusive; or
(f) an alkyl or haloalkyl of 2 to 4 carbon atoms, inclusive, which can be straight chain or branched.

In another embodiment of this invention, the lipoxin analogs have the structural formula IX:

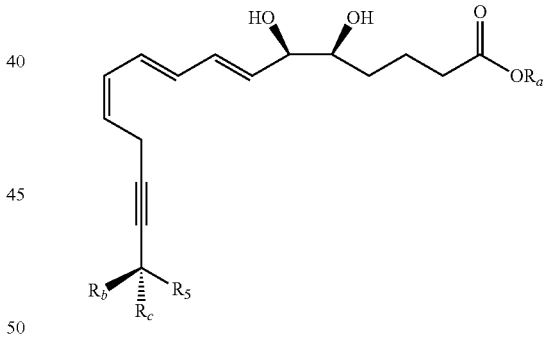

wherein $R_a$ is
(a) a hydrogen atom; or
(b) an alkyl of 1 to 8 carbon atoms;
wherein $R_b$ and $R_c$ are each independently:
(a) a hydrogen atom;
(b) a hydroxyl or thiol;
(c) a halomethyl;
(d) a halogen;
(e) an alkyl of 1 to 3 carbon atoms, inclusive, straight chain or branched;
(f) an alkoxy of 1 to 3 carbon atoms, inclusive; and
wherein $R_5$ is
(a) an alkyl of 1 to 9 carbon atoms which can be straight chain or branched;
(b) —$(CH_2)_n$—$R_i$
wherein n=0 to 4 and $R_i$ is (i) a cycloalkyl of 3 to 10 carbon atoms, inclusive;

(ii) phenyl; or (iii) substituted phenyl

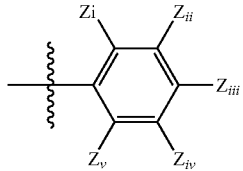

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) $R_aQ_aR_b$ wherein $Q_a$ is —O— or —S—;

wherein $R_a$ is alkylene of 0 to 6 carbons atoms, inclusive, which can be straight chain or branched;

wherein $R_b$ is either alkyl of 0 to 8 carbon atoms, inclusive, which can be straight chain or branched or substituted phenyl;

(d) —C($R_{iii}$)($R_{iv}$)—$R_i$ wherein $R_{iii}$ and $R_{iv}$ are each, independently:

(i) a hydrogen atom; or (ii) $CH_aZ_b$ where a+b=3, a=0 to 3, b=0+3 wherein each Z, independently, is a cyano, a nitro, or a halogen atom; or (e) haloalkyl of 1 to 8 carbon atoms, inclusive, and 1 to 6 halogen atoms, inclusive, straight chain or branched.

In another preferred embodiment, the compounds have the structural formula X:

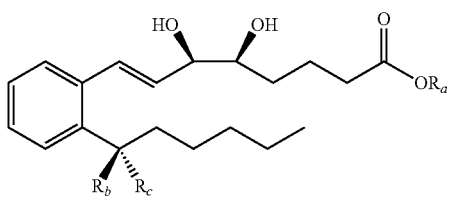

wherein $R_a$ is (a) a hydrogen atom; or (b) alkyl of 1 to 8 carbon atoms, inclusive, straight chain or branched; and wherein $R_b$ and $R_c$ are each, independently:

(a) a hydrogen atom;

(b) a hydroxyl or a thiol;

(c) a halomethyl;

(d) a halogen;

(e) an alkyl of 1 to 3 carbon atoms, inclusive, straight chain or branched;

(f) an alkoxy of 1 to 3 carbon atoms, inclusive.

In another preferred embodiment, the compounds have the structural formula XI:

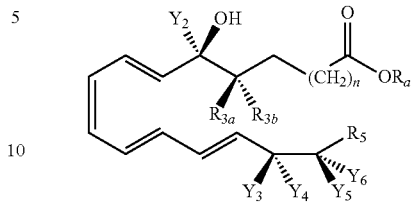

wherein $R_a$ is (i) a hydrogen atom;

(ii) an alkyl of 1 to 8 carbons atoms, inclusive, which can be straight chain or branched; or (iii) a detectable label molecule;

wherein n=1 to 10, inclusive;

wherein $Y_2$, $R_3a$, and $R_3b$ are each, independently:

(a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is —O— or —S—;

wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;

wherein $Y_1$ is —OH, methyl, or —SH;

wherein $Y_2$ is (a) a hydrogen atom;

(b) $CH_aZ_b$ where a+b=3, a=0 to 3, b=0 to 3 wherein each Z, independently, is a cyano, a nitro, or a halogen atom; or (c) an alkyl of 2 to 4 carbon atoms, inclusive, straight chain or branched;

wherein $Y_3$ and $Y_5$ are each independently:

(a) a hydrogen atom;

(b) $CH_aZ_b$ wherein a+b=3, a=0 to 3, b=0 to 3 and wherein each Z, independently, is a cyano, a nitro, or a halogen atom; or (c) an alkyl of 2 to 4 carbon atoms, inclusive, straight chain or branched;

wherein $Y_4$ and $Y_6$ are each, independently (a) a hydrogen atom;

(b) an alkyl of 2 to 4 carbon atoms, inclusive, straight chain or branched;

(c) an alkoxy of 1 to 4 carbon atoms, inclusive, straight chain or branched; or (d) a hydroxyl or thiol; and wherein $R_5$ is (a) an alkyl of 1 to 9 carbon atoms which can be straight chain or branched;

(b) —$(CH_2)_n$—$R_i$ wherein n=0 to 3 and $R_i$ is (i) a cycloalkyl of 3 to 10 carbon atoms, inclusive;

(ii) phenyl;

(iii) substituted phenyl

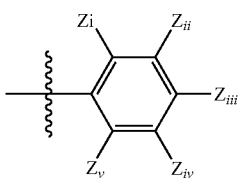

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) —$R_aQ_aR_b$
wherein $Q_3$ is —O— or —S—;
wherein $R_a$ is alkylene of 0 to 6 carbons atoms, inclusive, which can be straight chain or branched;
wherein $R_b$ is
(a) a substituted phenyl

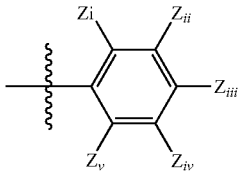

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(b) a substituted phenoxy

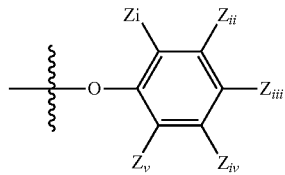

wherein $Z_i$ through $Z_v$ are as defined above; or

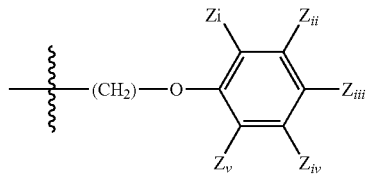

wherein $Z_i$ through $Z_v$ are as defined above;

(d) a haloalkyl of 1 to 8 carbon atoms, inclusive, and 1 to 6 halogen atoms, inclusive, straight chain or branched.

In certain embodiments of this invention, the compounds of this invention have the following structural formulas:

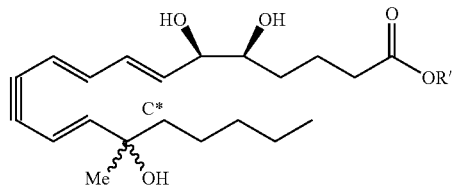

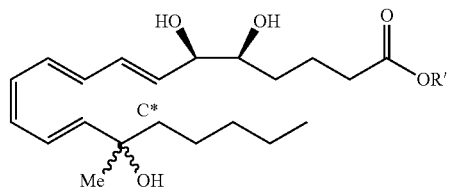

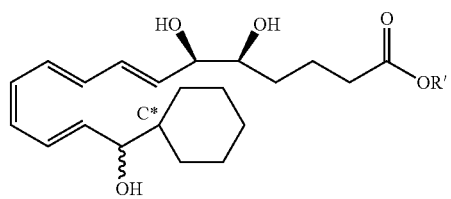

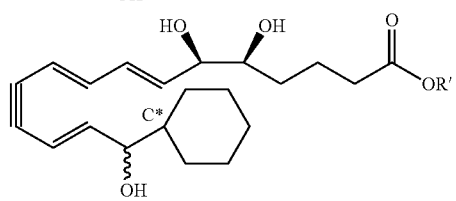

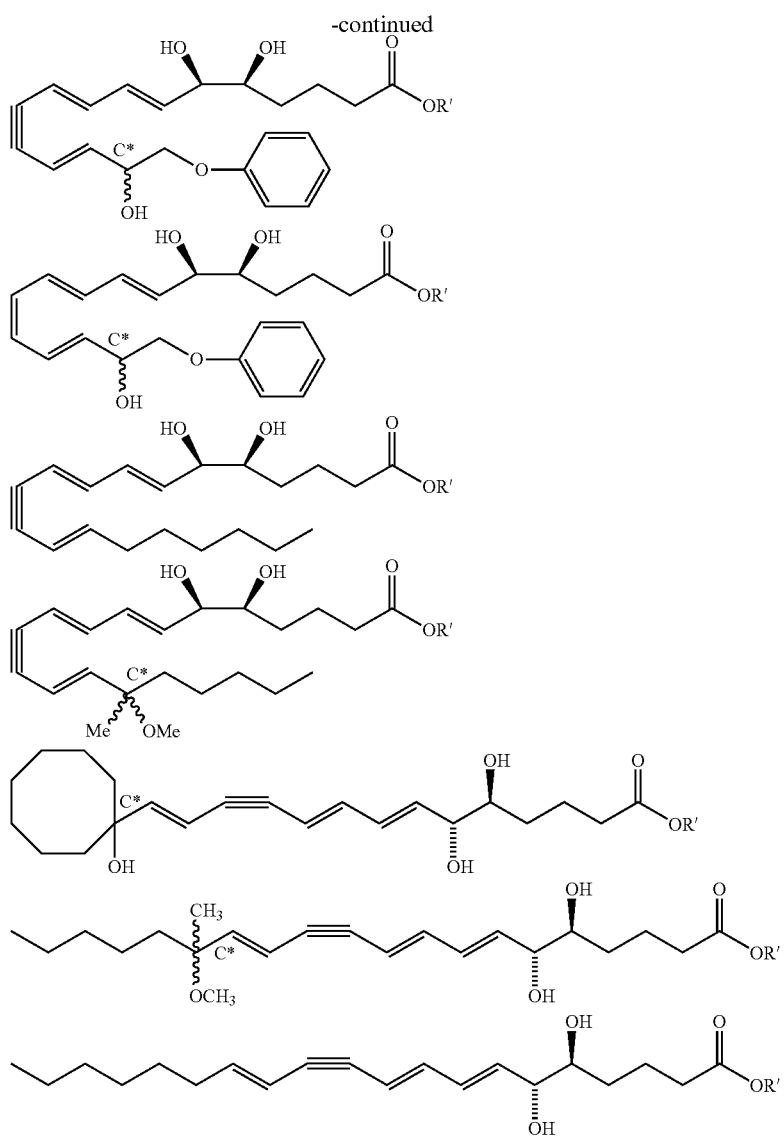
where R' is H or CH$_3$; and where the substituents at C* are in the R configuration.
In other preferred embodiments of this invention, the compounds of this invention have the following structural formulas:
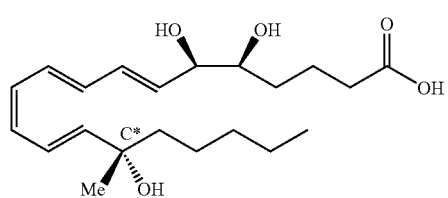
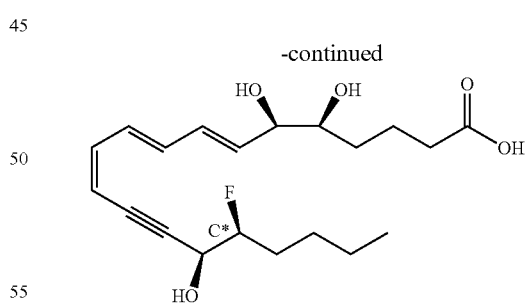
-continued
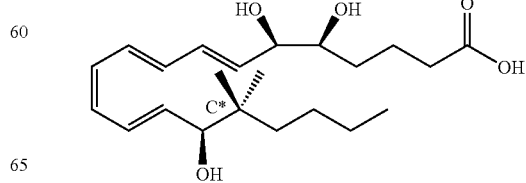

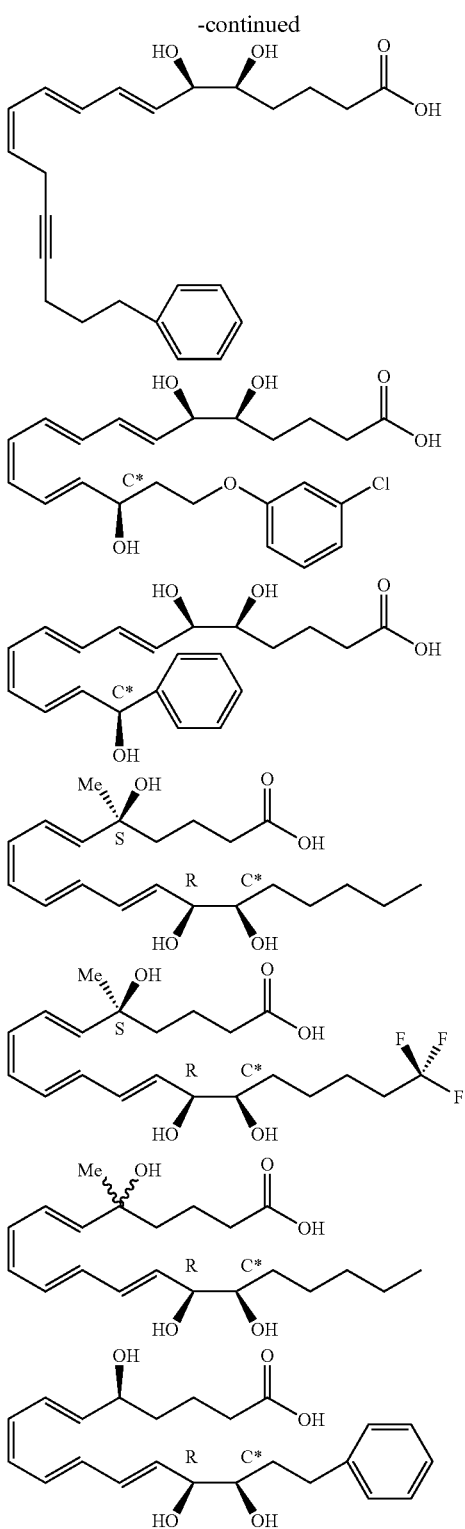

where the substituents at the C* are in the R configuration.

It is to be understood that the carboxylic acids and esters of the invention can be converted, if necessary, into pharmaceutically acceptable salts.

In certain embodiments of the invention, LXB$_4$ or the C5 and C14 and C15 alkanoates (acetates) of LXB$_4$ may be excluded.

Lipoxins Having Phenoxy or Thiophenoxy Substituents

In another aspect, lipoxins and lipoxin analogs useful as therapeutic agents in the treatment of the maladies, disease states or conditions described throughout the specification has the formula:

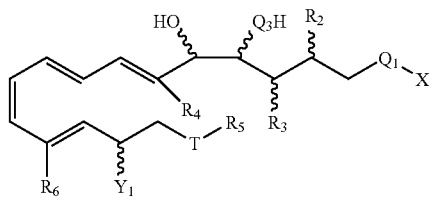

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

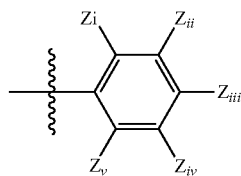

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;

wherein $R_5$ is

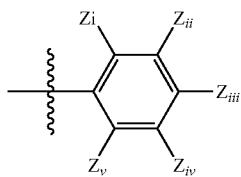

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof.

In yet another aspect, lipoxins and lipoxin analogs useful as therapeutic agents in the treatment of the maladies, disease states or conditions described throughout the specification has the formula:

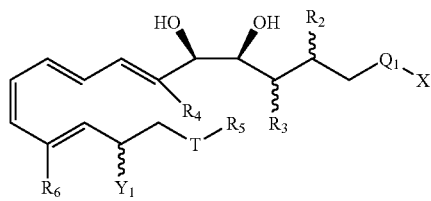

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

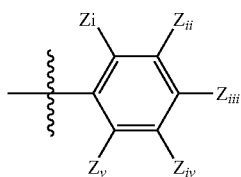

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;

(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;
wherein $R_5$ is

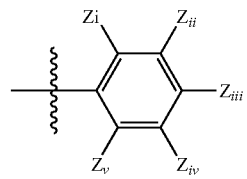

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof.

In still another aspect, lipoxins and lipoxin analogs useful as therapeutic agents in the treatment of the maladies, disease states or conditions described throughout the specification has the formula:

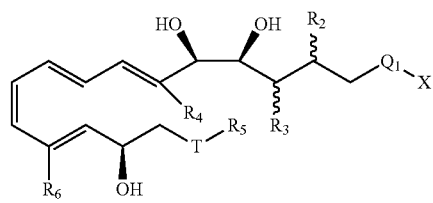

wherein X is $R_1$, $OR_1$, or $SR_1$;
wherein $R_1$ is (i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

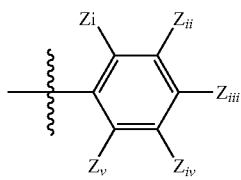

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_a Q_2 R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;
wherein $R_5$ is

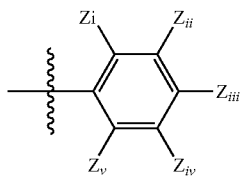

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;

wherein T is O or S, and pharmaceutically acceptable salts thereof.

In yet another aspect, lipoxins and lipoxin analogs useful as therapeutic agents in the treatment of the maladies, disease states or conditions described throughout the specification has the formula:

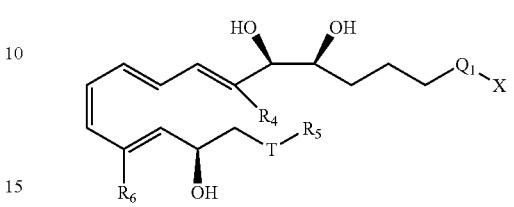

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

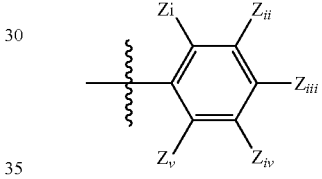

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_4$ is
(a) H;
(b) an alkyl of 1 to 6 carbon atoms, inclusive, which may be a straight chain or branched;
wherein $R_5$ is

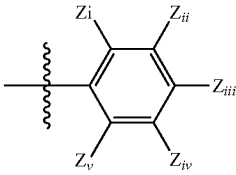

wherein $Z_i$, $Z_{ii}$, $Z_{iii}$, $Z_{iv}$ and $Z_v$ are each independently selected from —$NO_2$, —CN, —C(=O)$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
(a) H;
(b) an alkyl from 1 to 4 carbon atoms, inclusive, straight chain or branched;
wherein T is O or S, and pharmaceutically acceptable salts thereof.

In one aspect, lipoxins and lipoxin analogs useful as therapeutic agents in the treatment of the maladies, disease states or conditions described throughout the specification has the formula:

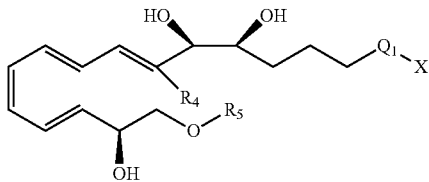

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

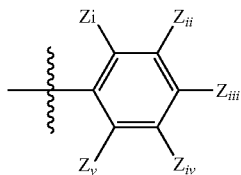

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $R_4$ is
(a) H;
(b) an alkyl of 1 to 6 carbon atoms, inclusive, which may be a straight chain or branched;
wherein $R_5$ is

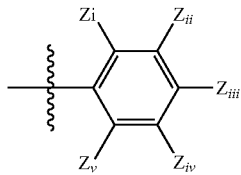

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group; and
pharmaceutically acceptable salts thereof.

In preferred embodiments, X is $OR_1$ wherein $R_1$ is a hydrogen atom, an alkyl group of 1 to 4 carbon atoms or a pharmaceutically acceptable salt, $Q_1$ is $C=O$, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

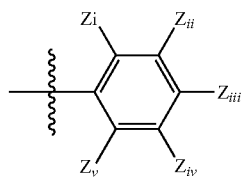

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl. In certain embodiments for $R_5$, para-fluorophenyl and/or unsubstituted phenyl are preferred, e.g., 15-epi-16-(para-fluoro)-phenoxy-$LXA_4$, 16-(para-fluoro)-phenoxy-$LXA_4$, 15-epi-16-phenoxy-$LXA_4$ or 16-phenoxy-$LXA_4$.

In still another aspect, the present invention is directed to pharmaceutical compositions including compounds having the formulae described throughout the specification and a pharmaceutically acceptable carrier. In one embodiment, a preferred compound is

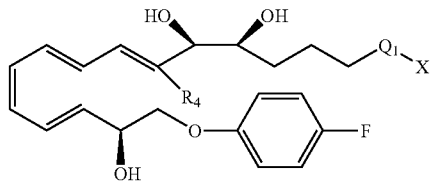

In one embodiment, $Q_1$ is a carbonyl, X is a hydroxyl or an $-OR$, wherein R is an alkyl group, i.e., methyl or ethyl groups, and $R_4$ is a hydrogen atom.

In other embodiments, $Y_1$ is a hydroxyl and the carbon bearing the hydroxyl can have an R or S configuration. In most preferred embodiments, the chiral carbon bearing the hydroxyl group, e.g., $Y_1$ is designated as a 15-epi-lipoxin as is known in the art.

In certain embodiments the chirality of the carbons bearing the $R_2$, $R_3$, $Q_3$ and $Q_4$ groups can each independently be either R or S. In preferred embodiments, $Q_3$ and $Q_4$ have the chiralities shown in above-referenced structures.

In preferred embodiments, $R_4$ is a hydrogen. In other preferred embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds useful in the present invention can be prepared by the following synthetic scheme:

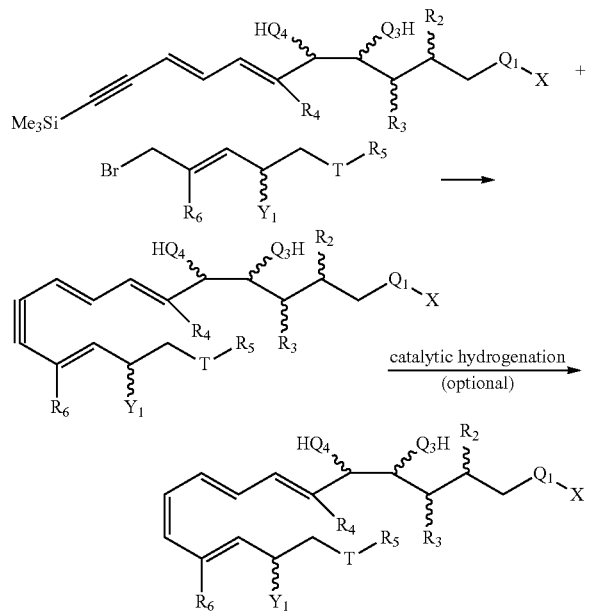

wherein X, $Q_1$, $Q_3$, $Q_4$, $R_2$, $R_3$, $R_4$, $R_5$, $R_6$, $Y_1$ and T are as defined above. Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263. As a consequence, the acetylenic intermediates are also encompassed by the present invention as being useful for the treatments of the various maladies described herein. Similar approaches can be taken to produce $LXB_4$ acetylenic compounds as described in, for example, U.S. Pat. No. 6,316,648.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as leukotriene C4 and/or leukotriene D4), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. For example, lipoxin $A_4$ analogs have an active region comprising $C_5$-$C_{15}$ of natural lipoxin $A_4$. Similarly, for example, lipoxin $B_4$ analogs have an active region comprising C5-C14 of natural lipoxin $B_4$.

The term "recognition site" or receptor is art-recognized and is intended to refer generally to a functional macromolecule or complex of macromolecules with which certain groups of cellular messengers, such as hormones, leukotrienes, lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. Similarly, such regions are possibly located within ATL and $LXB_4$ analogs. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled analog" is further understood to encompass compounds which are labeled with radioactive isotopes, such as but not limited to tritium ($^3H$), deuterium ($^2H$), carbon ($^{14}C$), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native eicosanoid. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite. Similarly, this also applies to ATL and $LXB_4$ analogs.

The term "resists metabolism" is meant to include failing to undergo one or more of the metabolic degradative transformations by at least one of the enzymes which metabolize lipoxins, ATL or $LXB_4$ analogs. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin, lipoxin analogs, ATL or $LXB_4$ analogs. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

Materials and Methods

Cell Culture

Human umbilical vein endothelial cells (HUVEC) were isolated by 0.1% collagenase digestion (Worthington Biochemical, Bedford, Mass.) and propagated on gelatin-coated (0.1%) tissue culture plates in medium 199 (Gibco BRL, Grand Island, N.Y.) supplemented with 20% heat-inactivated fetal bovine serum (BioWhittaker, Walkersville, Md.), 50 µg/ml of endothelial cell mitogen (Biomedical Technologies, Stoughton, Mass.), 8 U/ml heparin (APP, Los Angeles, Calif.), 50 U/ml penicillin and 15 µg/ml streptomycin. Only passages 2 and 3 were used in reported experiments.

Endothelial Cell Proliferation

HUVEC ($5 \times 10^3$) were plated in 96-well plates coated with 0.1% gelatin for 1 h at room temperature. After 24 h, the medium was removed and replaced with fresh medium 199 supplemented with 5% fetal bovine serum and different concentrations of recombinant human $VEGF_{165}$ (R&D Systems, Minneapolis, Minn.), $LTD_4$ or $LTB_4$. Endothelial cells were enumerated after 72 h using the MTT® assay (Sigma, St. Louis, Mo.) (15). ATL-1 was prepared as in Clish et al. (13). Percent inhibition was evaluated in a similar manner and included a 15 minute incubation (37° C.) with 15-epi-lipoxin $A_4$, 15-epi-16-(para-fluoro)-phenoxy-lipoxin $A_4$ methyl ester (ATL-1), $LXA_4$, 15-epi-$LXA_4$ or 15-R/S-methyl, $LXA_4$ prior to the addition of agonists. All incubations were performed in triplicate. Before each experiment the integrity and concentration of ATL-1, $LXA_4$, 15-epi-$LXA_4$ or 15-R/S-methyl, $LXA_4$ was assessed by physical methods including LC/MS/MS and UV (13).

Endothelial Cell Migration

VEGF, ATL-1 or vehicle were added to the lower wells of a 48-well-chemotaxis chamber (NeuroProbe, Cabin John, Md.). The wells were overlaid with a 10 µm pore size polycarbonate filter coated with 0.1% gelatin. HUVEC ($1 \times 10^6$) were placed in the upper wells and the chamber was incubated (37° C., 5% $CO_2$ for 12 h). Following incubations, filters were removed, scraped of cells from the upper surface, fixed and stained with Diff-Quik (Dade Behring, Newark, Del.). Cells that migrated across the filter toward the lower surface were enumerated by light microscopy; four fields were counted at high magnification (100×). Incubations were performed in triplicate. To assess inhibition, endothelial cells were suspended in media with vehicle or ATL-1 for 15 min before placement in the chamber.

Quantitative Determination of DNA Fragmentation

DNA fragmentation in individual apoptotic cells was quantitated using a photometric enzyme immunoassay (Apoptosis detection kit: R&D Systems). HUVECs grown in 96-well microtiter plates ($5 \times 10^3$ cells/well) were incubated for 3 days, fixed with 3.7% formaldehyde, and permeabilized with proteinase K before the labeling. Biotinylated nucleotides are incorporated onto the DNA fragments and detected by using steptavidin-horseradish peroxidase conjugate followed by the substrate TACS-Sapphire.

Inflammatory Angiogenesis

Angiogenesis was assessed with murine air pouches that were raised via subcutaneous injection of sterile air (3 ml) beneath the dorsal skin of anesthetized mice (BALB/c, male 6-8 wk). After 24 hrs, ATL-1 (10 µg/pouch) or vehicle was delivered locally, immediately before the injection of VEGF (1 µg/pouch). The vascular content was assessed by the formation of vascular casts (as in 16). Briefly, mice were anesthetized (at 144 h) and peripheral vasodilation was raised by placing the animals in a heated jacket (40° C., 10 min). Vascular casts were formed by the i.v. injection of 1 ml 5% carmine red (Sigma) in 5% gelatin solution warmed to 40° C. Air pouch linings were dissected and weighed. The tissue was then dissolved in 2 ml of 3 N NaOH solution for 0.5 h, 21° C. and completely digested in hot water (56° C.) for 10 min. Digested samples were centrifuged (2500 rpm, 15 min) and filtered through a 0.45 µm filter. The dye content was quantified employing a 96-well plate spectrophotometer at 530 nm using a calibration curve. The results were expressed as vascular index (VI) as micrograms carmine dye/milligram weight of tissue, for n=4 animals/group. For visualization of the vasculature, the dorsal surface of the pouches was excised and fixed in formalin for 48 h. The tissues were dehydrated with 100% ethanol (5 days, 4° C.) and cleared by immersion in cedar wood oil for 2 weeks. In another set of experiments, mice were anesthetized and injected i.v. with 200 µl of 0.05 g/ml fluorescein isothiocyanate-dextran (Sigma) in PBS at 144 h immediately-before sacrifice. Dissected linings were fixed, mounted on glass slides and examined for fluorescence (Nikon Eclipse model E600). In both protocols, the observers were not blinded to the treatments.

Immunohistochemistry

Air pouch membranous tissues were fixed in 10% buffered formalin overnight and processed for paraffin embedding. Five-micrometer paraffin sections of membrane tissue cut on face were used for immunohistochemistry for CD31 expression. Briefly, slides were deparaffinized and pretreated in 0.25% trypsin (Sigma Chemical) for 20 min at 37° C., followed by washing in distilled water. All further steps were performed at room temperature in a hydrated chamber. Slides were pretreated with Peroxidase Block (DAKO, Carpinteria, Calif.) for 5 min to quench endogenous peroxidase activity, followed by a 1:5 dilution of goat serum in 50 Mm Tris-Cl, pH 7.4, for 20 min to block nonspecific binding sites. Primary rat anti-murine CD31 antibody (BD PharMingen, San Diego, Calif.) was applied at a 1:100 dilution in 50 mMTris-Cl, pH 7.4, with 3% goat serum for 1 h. After washing in 50 mM Tris-Cl, pH 7.4, secondary rabbit anti-rat antibody (DAKO)

was applied at a 1:200 dilution in 50 mM Tris-Cl, pH 7.4, with 3% goat serum for 30 min. Slides were washed again in 50 mM Tris-Cl, pH 7.4, and goat anti-rabbit horse-radish peroxidase-conjugated antibody (Envision detection kit: DAKO) was applied for 30 min. After further washing, immunoperoxidase staining was developed using a DAB chromogen kit (DAKO) per the manufacturer and counterstained with hematoxylin.

Statistical Analysis

Results are presented as means±S.E.M. Statistical evaluation of the results was performed by analysis of variance, and values of $P<0.05$ were taken to represent statistically significant differences between group means.

Results and Discussion

The aspirin-triggered lipoxin $A_4$ stable analog (denoted ATL-1) proved a potent inhibitor of VEGF-stimulated proliferation of HUVECs ($IC_{50}$ of ~3 nM) (FIG. 1). Inhibition was concentration-dependent and maximal plateau at 10 nM and was partially reversed (from 38.0±2.5 to 78.0±6.21% of VEGF-stimulated proliferation, $P<0.05$) by incubating the cells with genistein, an inhibitor of tyrosine kinase activity (50 μM, 5 min, 37° C., n=3). Even at high concentrations (100 μM), the ATL-1 analog alone had no apparent actions on HUVEC proliferation (FIG. 1 inset). In sharp contrast, $LXB_4$ stable analogs increased proliferation. Because these are related structures, the separate actions of ATL and $LXB_4$ analogs with these cells indicate that the ATL-1 response is highly stereoselective. Also, a direct comparison of ATL-1 with native $LXA_4$ and 15-epi-$LXA_4$ at equimolar concentrations (10 nM) in a representative experiment showed that ATL-1>15-epi-$LXA_4$>$LXA_4$ in rank order of activity (e.g., 63.3±3.3, 59.8±1.8 and 38.1±2.0% inhibition, respectively). After exposure of the cells to ATL-1, ~98% of the HUVEC remained viable, as determined by trypan blue exclusion assay, indicating that the compound was not cytotoxic. In addition to being an endothelial cell-specific mitogen, VEGF is also an endothelial cell survival factor, thus promoting angiogenesis not only by stimulating cell proliferation but also by inhibiting endothelial cell apoptosis (17).

To determine whether this new inhibitory action of ATL-1 on HUVEC proliferation involved apoptosis, DNA fragments were quantitated (under Materials and Methods). Neither the ATL-1 (100 nM) alone nor in combination with VEGF (3 ng/ml) affected DNA fragmentation pattern (n=2, d=3), suggesting that the antiproliferative actions of the ATL-1 analog were not a results of induction of apoptosis in endothelial cells. Binding of αv integrins by endothelial cells is accompanied by a decrease in the tumor-suppressor p53 activity and inhibition of apoptotic pathways, thereby facilitating the formation of new blood vessels (18). Along these lines, it was recently shown that p53 can up-regulate human 15-lipoxygenase promoter activity, providing the first link between this enzyme's activity and an established tumor-suppressor gene (19). Also of interest, over-expression of 15-lipoxygenase enhances endogenous $LXA_4$ formation that in turn inhibits progression of glomerulonephritis (20). Both ATL and $LXA_4$ share sites of action that are receptor cell type, and tissue-specific, and together with their stable analogs display potent anti-inflammatory actions (21, 23 and 14).

Figure 2:
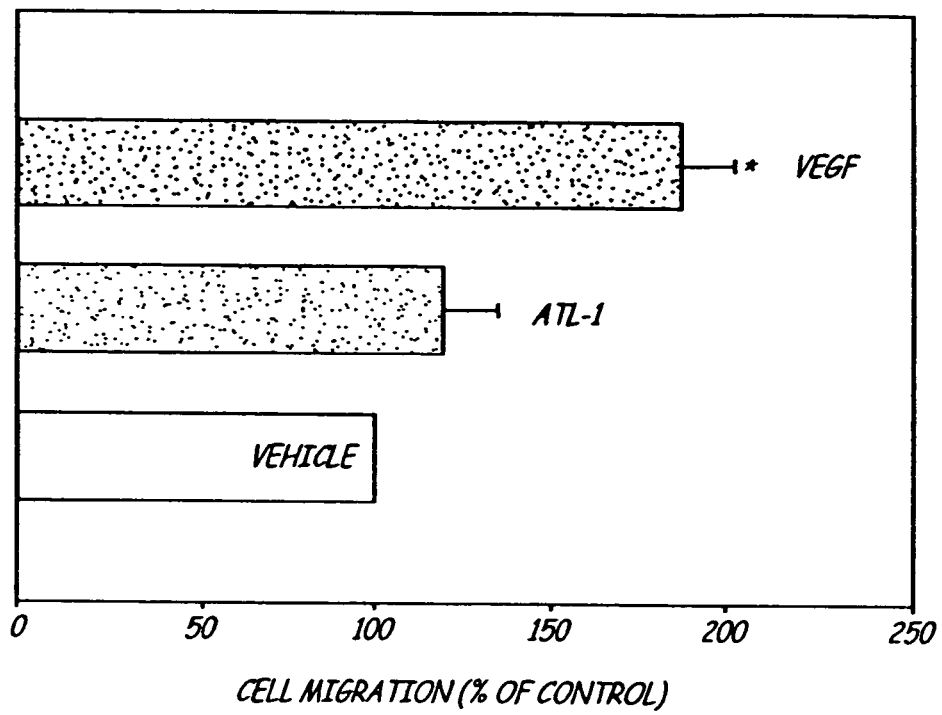
FIG. 2 demonstrates that ATL-1, as well as LXA$_4$, 15-epi-LXA$_4$ and 15-R/S-methyl, LXA$_4$ each inhibit endothelial cell chemotaxis. (A) Chemotaxis was initiated by addition of VEGF (3 ng/ml) or ATL-1 (100 nM) to the lower compartment of a 48-well chemotaxis chamber. Results are expressed as percent of cell migration compared to vehicle alone and represent mean±SE for three independent experiments performed in triplicate (P<0.05). (B) HUVEC were incubated with vehicle or indicated concentrations of ATL-1 (15 min, 37° C.) and added to the upper compartment of the microchamber ($1 \times 10^6$/well). Chemotaxis was initiated by addition of VEGF (3 ng/ml) to the lower compartment. Results are expressed as percent inhibition of migration relative to VEGF for a representative experiment performed in triplicate.
Figure 2:
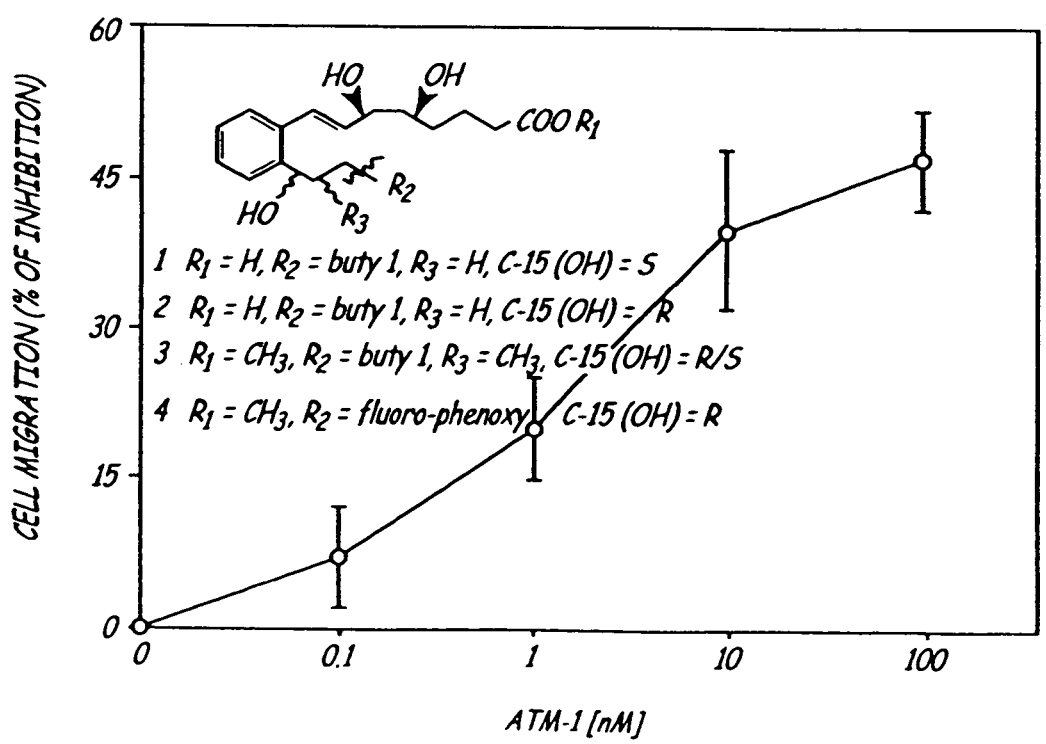

Endothelial cell migration is an essential component of the angiogenic process, providing directionality for the budding capillary toward the angiogenic stimulus (3). Therefore, endothelial migration was assessed with ATL. VEGF (3 ng/ml) was added to the lower compartment of a chemotaxis chamber and cell migration across a 10-μm pore-size gelatin-coated filter was quantitated (FIG. 2). Results in FIG. 2B showed that ATL-1, $LXA_4$, 15-epi-$LXA_4$ and 15-R/S-methyl, $LXA_4$ (ATL-1 shown as representative) gave concentration-dependent inhibition of VEGF-stimulated HUVEC migration with a maximum level of inhibition (~45%) at 10 nM ATL. As observed with proliferation assays, ATL-1, $LXA_4$, 15-epi-$LXA_4$ or 15-R/S-methyl, $LXA_4$ alone, even at higher concentrations (100 nM), did not induce endothelial cell migration (FIG. 2A), findings which suggest that ATL, $LXA_4$, 15-epi-$LXA_4$ or 15-R/S-methyl, $LXA_4$ play a role in blocking the early stages of cell migration to sites of neovascularization.

Figure 3A:
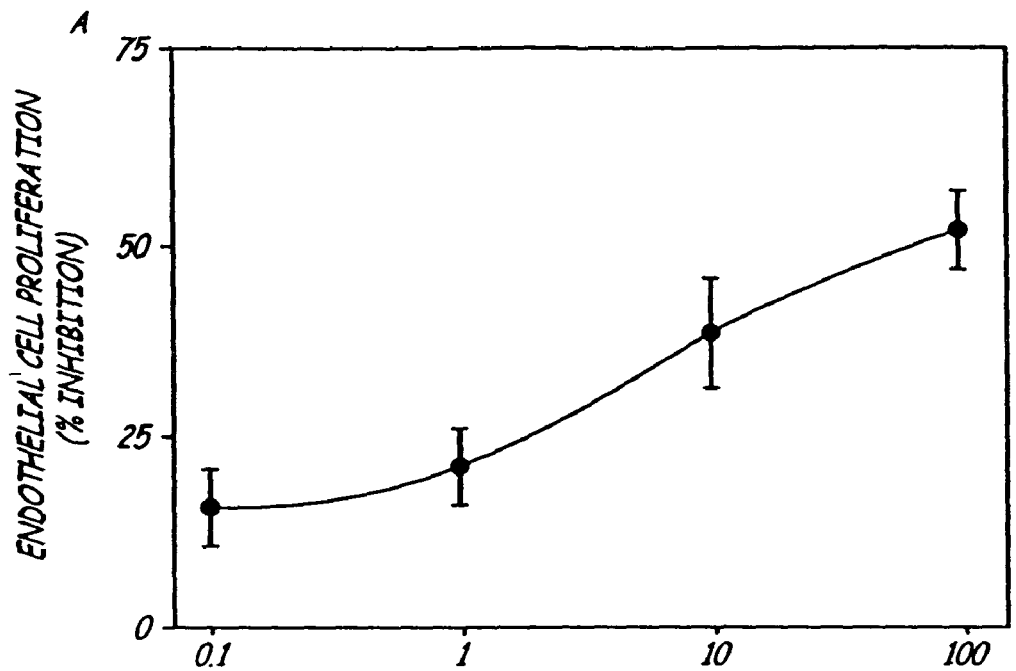
FIG. 3 is a graphical representation demonstrating inhibition of HUVEC proliferation. (A) ATL-1 inhibits LTD$_4$-stimulated HUVEC proliferation. HUVECs ($5 \times 10^3$) were plated in 96-well culture plates, cell proliferation was stimulated with 10 nM LTD$_4$, and cell numbers were determined after 3 days using MTT. (B), concentration dependent cell proliferation induced by LTD$_4$ and LTB$_4$. Results are expressed as mean±S.E. for four independent experiments performed in triplicate.
Figure 3B:
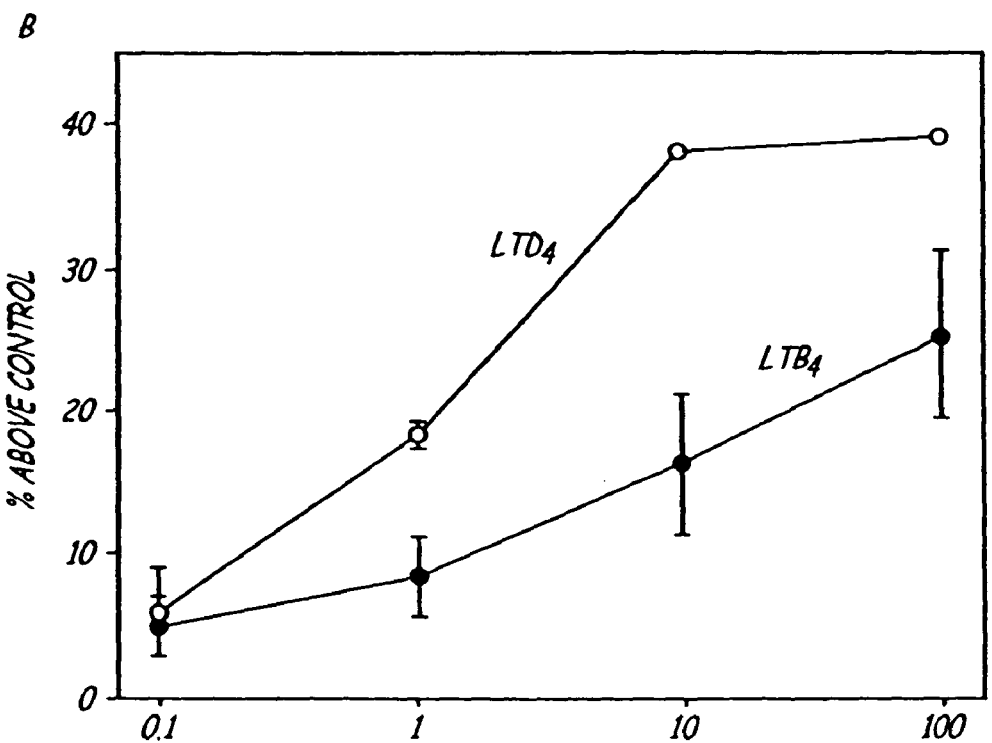

Like VEGF (FIG. 1). $LTD_4$ also stimulated proliferation of HUVEC (42±1.2%) with a maximum at 10 nM, similar to the response obtained with VEGF (52.7±1.6%)). In contrast, $LTB_4$ at 10 nM did not give a significant response with these cells (FIG. 3B). The mitogenic action of $LTD_4$ (10 nM) was antagonized by exposure of the cells to ATL-1 (0.1-100 nM) with an $IC_{50}$ of ~3 nM (FIG. 3A). $LTD_4$ did not enhance or inhibit the VEGF-stimulated proliferation.

The antiproliferative actions of native lipoxins were first found with the human lung adenocarcinoma cell line (23) and recently with human renal mesangial cells (24). The present findings, together with endothelial cell results, draw attention to the potential regulatory role for endogenous ATL in proliferative diseases. The actions of LX, ATL and stable analogs are transduced by a high affinity transmembrane receptor (ALXR) identified in several cell types (for a review, see Chiang et al. (25)). In mesangial cells, $LXA_4$ interacts with its own high affinity receptor (i.e., ALXR) as well as with a subclass of peptido-leukotriene receptors ($cysLT_1$), where $LXA_4$ is a partial agonist (24). In this regard, $LXA_4$ and its bioactive stable analogs effectively displace $[^3H]LTD_4$ specific binding to vascular endothelial cells (26). Also, recent findings provide the first evidence that ATL specifically antagonizes $LTD_4$ specific binding at recombinant human $cysLT_1$ cloned from endothelial cells, as well as acts at specific $LXA_4$ receptors (21). Since ATL-1 proved to be a potent inhibitor of HUVEC proliferation (FIGS. 1, 2 and 3), it was determined whether ATL affected angiogenesis in vivo.

During chronic inflammation, new vessels are required not only for the maintenance of tissue perfusion, but also to allow increased cellular traffic (27). Therefore, to this end angiogenesis was assessed in vivo using a well established murine chronic granulomatous air pouch model, and the 6-day time interval was selected because it was shown to give near maximal vascular density (16). ATL-1 injected locally (10 μg/pouch) immediately before the administration of VEGF (1 μg/pouch) gave a ~48% reduction in the vascular index (FIG. 4A). For comparison, ATL-1 (10 μg/mouse or 0.4 mg/kg mouse) proved to be much more potent than other described anti-angiogenic agents that required much higher doses, including steroids at 1-3 mg/kg (16), or the COX-2 inhibitors, which require 1-6 mg/kg (28).

Figure 4B:
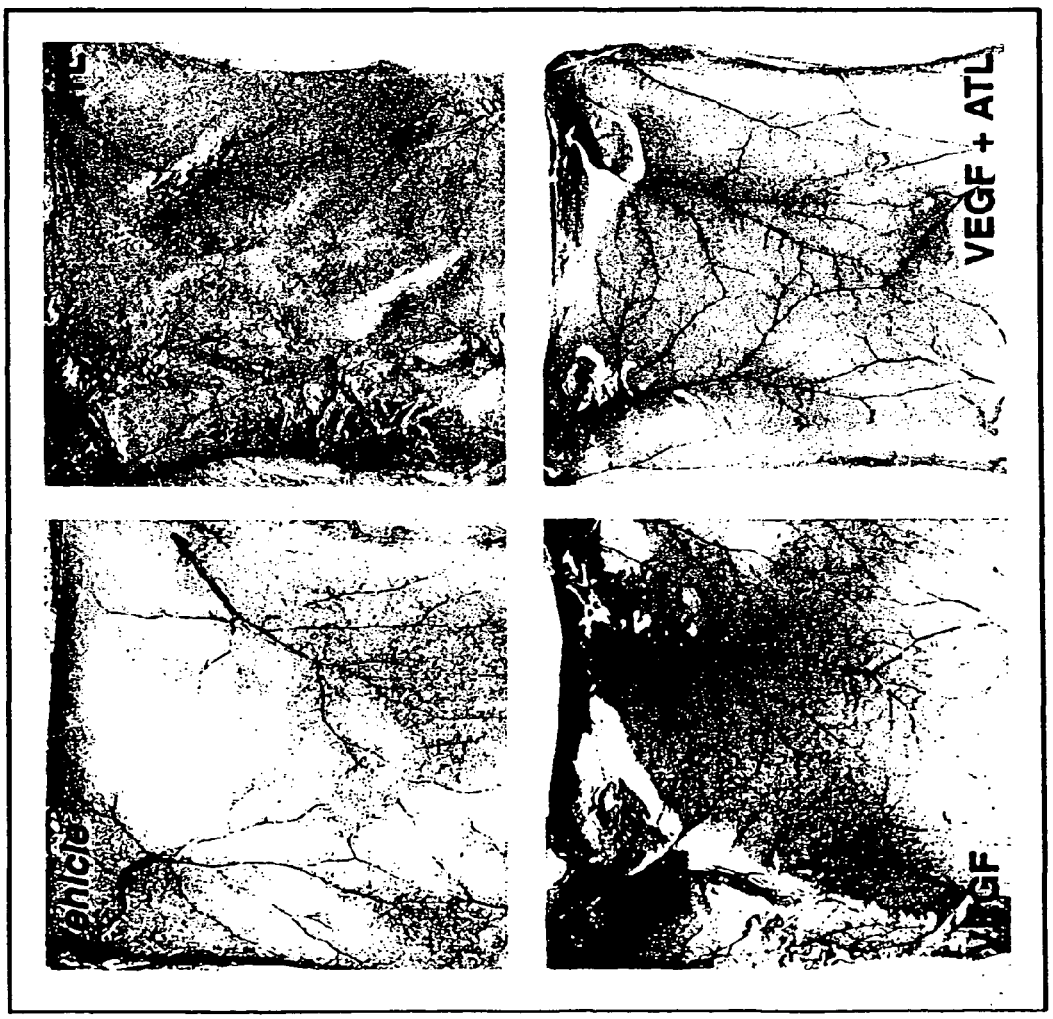
FIG. 4 demonstrates that ATL-1 inhibits angiogenic phenotype in vivo. (A) Vascular index (VI=mg carmine dye/mg weight of tissue) in day-6 murine air pouch. Animals received a local injection of ATL-1 (10 µg/pouch) or vehicle immediately before VEGF (1 µg/pouch), 24 h after raising the pouch. Results are expressed as the mean±SE for n=4 animals per group. *Denotes statistically significant difference (P<0.05) from VEGF alone; (B) Cedar wood oil histology of air pouch. Carmine dye vascular casts were made in day-6 air pouch from mice treated locally with vehicle, ATL-1 (10 µg), VEGF (1 µg) or VEGF plus ATL-1. Tissue was fixed in ethanol and cleared in cedarwood oil.

FIG. 4B shows representative vascular casts from typical day 6 air pouch linings. In the mice given VEGF (FIG. 4B, bottom left panel), there is an established neovasculature with an extremely high degree of vascular density compared to only slightly dilated capillaries in the ATL-treated animals, where there was routinely clearly reduced vascular density (FIG. 4B, bottom right panel). In another set of experiments, fluorescein isothiocyanate-dextran was used to visualize the vessels in this region. In sharp contrast to the actions of ATL-1, when $LTB_4$, another lipoxygenase pathway product, was given alone at the same dose as ATL-1 (10 μg $LTB_4$/pouch), $LTB_4$ stimulated neovascularization (n=2).

Figure 5:
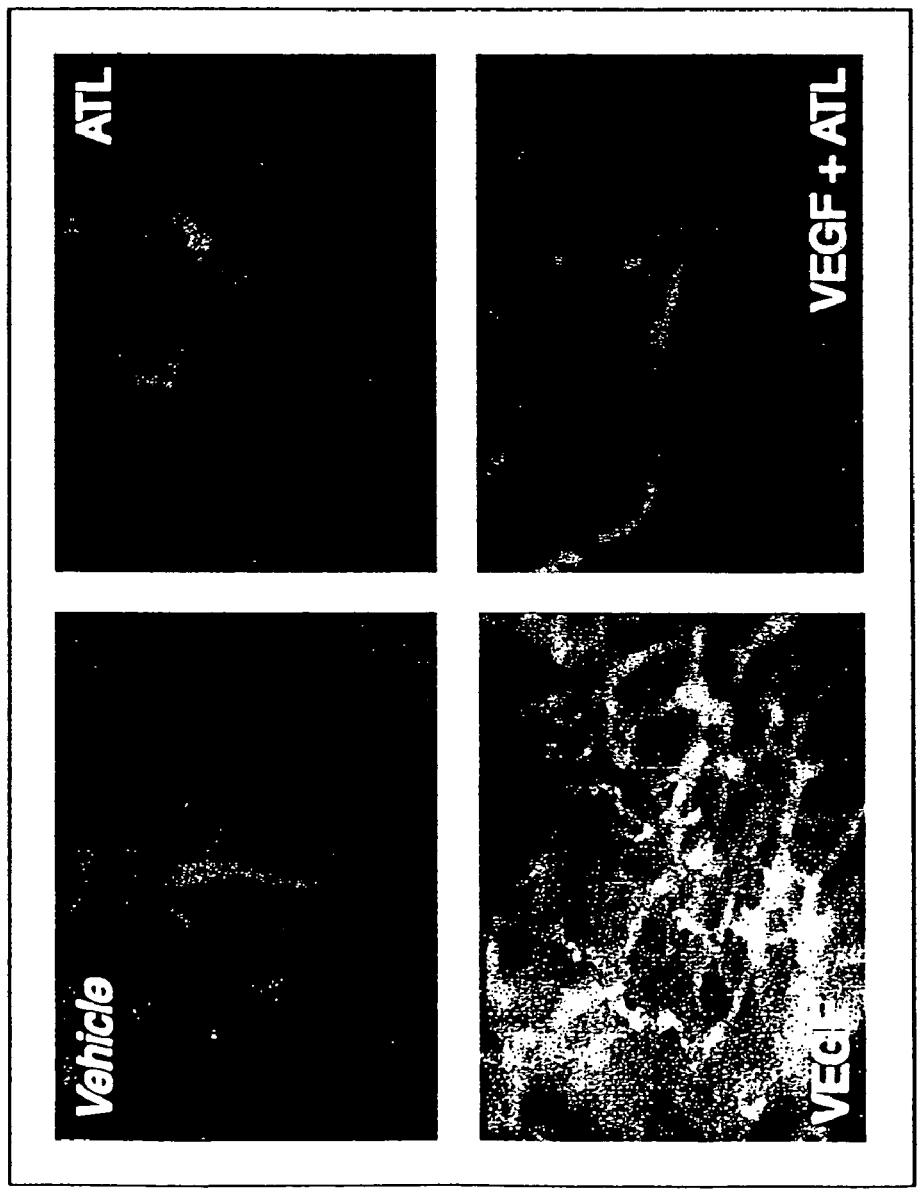
FIG. 5 depicts Anti-angiogenic action of ATL-1: fluorescent microscopy. Representative fluorescence photomicrographs showing the anti-angiogenic action of ATL-1 (10 µg/pouch) in the murine air pouch (see methods).

FIG. 5 shows photomicrographs of the dorsal linings dissected at day 6. Again, profound angiogenesis was demonstrated with extensive vascular networks in VEGF-treated pouch (FIG. 5, bottom left panel). Here too, treatment with ATL-1 (10 μg/pouch) gave striking reduction of VEGF-elicited vasculature, as exemplified by the lack of visible fine capillaries (FIG. 5, bottom right panel).

Figure 6:
FIG. 6 are photomicrographs of a murine air pouch. Immunohistochemistry for murine air pouch CD31. Paraffin-embedded air pouch sections were stained for CD31 from mice as in FIGS. 4 and 5 and treated with vehicle alone (A), analog alone (B), VEGF-treated mice (C), and VEGF plus ATL-treated mice (D). Results are representative of eight separate mice each in duplicate. Magnification is 200× power and horseradish peroxidase with hematoxylin counterstain.
Figure 6:
Figure 6:
Figure 6:
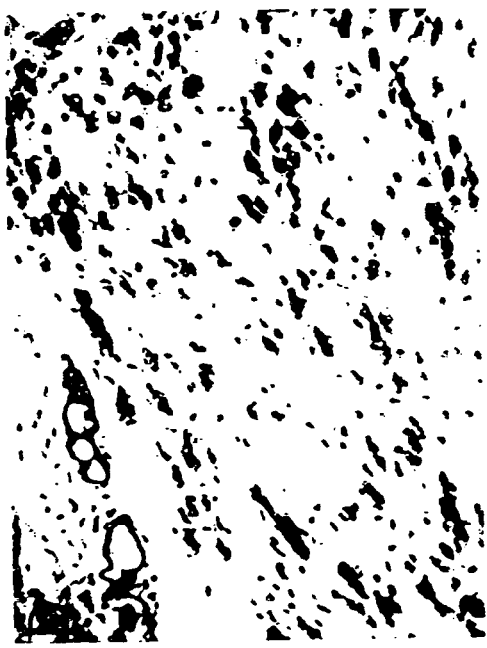

It is important to note that ATL-1 at this dose (10 μg/mouse i.v.) does not evoke apparent changes in mean arterial pressure, excluding a possible action of ATL-1 at the level of vascular tone. This is particularly noteworthy because, at high doses, $LXA_4$ can stimulate vasodilation in certain vascular beds. The present in vivo experiments were performed in separate series to evaluate histology and the presence of a vascular marker by using immunohistochemical staining of the murine air pouch with the vascular endothelial cell marker CD31 (FIG. 6).

Platelet/endothelial cell adhesion molecule-1 (or CD31) is a member of the Ig superfamily that is strongly expressed at the endothelial cell-cell junction, is present on platelets as well as leukocytes, and is held to play a role in angiogenesis and in transendothelial migration of leukocytes. Immunohistochemical staining for CD31 in the pouches showed that, in the VEGF-treated mice, strong specific endothelial cell staining was present and identified a prominent vascular network (FIG. 6C). In contrast, a marked diminution of vessels was observed in VEGF-treated mice that were also treated with the $LXA_4$ analog (FIG. 6D). The levels of mild nonspecific staining associated with these air pouches were essentially identical to those of the air pouch sections from mice treated with either vehicle alone (FIG. 6A) or with LX analog alone (FIG. 6B), namely, mild nonspecific staining of inflammatory cells, predominantly leukocytes and macrophages, that are known to be associated with these air pouches created from murine skin. Taken together, these findings indicate that ATL reduced VEGF-stimulated angiogenesis in vivo, suggesting that $LXA_4$ and 15-epi-$LXA_4$ can regulate these actions in vivo.

Results from many clinical and laboratory studies have demonstrated protective effects of aspirin in several forms of human cancer, including lung, colon and breast cancer, yet its potential anti-cancer mechanism is not clear (see Ref. 9). ASA is thought to act, in part, via reduction of angiogenesis, which might be related to the ability of ASA to inhibit prostanoid biosynthesis (7). More recently, ASA was found to trigger a novel switch in eicosanoid biosynthesis as the acetylation of COX-2 enables the enzyme to produce 15R-HETE that is converted to 15-epi-lipoxins, also known as ATL, during cell-cell interactions in vitro and in vivo (11, 12, 14). ATLs as well as their stable bioactive analogs are potent inhibitors of several key events in acute inflammation, such as PMN chemotaxis and transmigration across both endothelial and epithelial cells, as well as diapedesis from postcapillary venules (13, 14). The analogs of ATL mimic both endogenous ATL and LX actions and were designed to resist rapid enzymatic inactivation in vivo. Bioactive analogs of 15-epi-$LXA_4$ were also found to complete at both the ALXR on leukocytes and the $cysLT_1$ receptor present on vascular endothelial cells. In addition, these novel aspirin-triggered mediators inhibit cytokine release and can act at the gene transcriptional level (29) to redirect local cytokine-chemokine axis (30), actions that are both of interest in the angiogenic process (3). It should be noted that most if not all other eicosanoids examined to date are pro-angiogenic including leukotrienes (e.g., $LTD_4$ and $LTB_4$, see the following table and FIG. 3) (5, 6, 28). In view of this, it was surprising that ATL-1, $LXA_4$, 15-epi-$LXA_4$ and 15-R/S-methyl, $LXA_4$ possessed antiangiogenic activity.

$LXB_4$-Induced HUVEC Proliferation

| Compound | Percent of Proliferation |
| --- | --- |
| 14-epi-$LXB_4$ 0.1 nM | 15.5 ± 1.0 |
| 14-epi-$LXB_4$ 1.0 nM | 18.3 ± 1.6 |
| 14-epi-$LXB_4$ 10 nM | 27.0 ± 5.0 |
| 14-epi-$LXB_4$ 100 nM | 27.7 ± 1.3 |
| 15-epi-$LXB_4$ 0.1 nM | 20.1 ± 1.2 |
| 15-epi-$LXB_4$ 1.0 nM | 26.1 ± 2.8 |
| 15-epi-$LXB_4$ 10 nM | 34.0 ± 2.5 |
| 15-epi-$LXB_4$ 100 nM | 35.2 ± 5.2 |
| 15-epi-$LXB_4$-acetylenic 0.1 nM | 18.7 ± 1.6 |
| 15-epi-$LXB_4$-acetylenic 1.0 nM | 23.7 ± 0.4 |
| 15-epi-$LXB_4$-acetylenic 10 nM | 36.4 ± 3.7 |
| 15-epi-$LXB_4$-acetylenic 100 nM | 37.4 ± 5.3 |

VEGF-Induced Proliferation: 50.4±4.0

In summary, the present results demonstrate that an aspirin-triggered-lipoxin, 15-epi-$LXA_4$ analog, is a potent inhibitor of angiogenesis and of endothelial cell proliferation in vivo. Together these results reveal a novel action of 15-epi-lipoxins and suggest a role for the aspirin-triggered lipoxin circuit (14) as a potential mechanism that can contribute to aspirin's recognized anti-angiogenic and anti-inflammatory properties (2, 7, 10). With increasing insight into the fundamental role of angiogenesis within a broad range of physiological as well as disease processes (1-3), the modulation of vascular growth could be a previously unappreciated and important strategic action for ATL, the natural endogenous lipoxin mimetic and their synthetic analogs.

REFERENCES

1. Folkman, J., and Y. Shing. 1992. Angiogenesis. *J. Biol. Chem.* 267:10931-10934.
2. Folkman, J. 1995. Angiogenesis in cancer, vascular, rheumatoid and other disease. *Nature Med.* 1:27-31.
3. Arenberg, D. A., and R. M. Strieter. 1999. Angiogenesis. In Inflammation: Basic Principles and Clinical Correlates. J. I. Gallin and R. Snyderman, editors. Lippincott Williams & Wilkins, Philadelphia. 851-864.
4. Höper, M. M., N. F. Voelkel, T. O. Bates, J. D. Allard, M. Horan, D. Shepherd, and R. M. Tuder. 1997. Prostaglandins induce vascular endothelial growth factor in a human monocytic cell line and rat lungs via cAMP. *Am. J. Respir. Cell Mol. Biol.* 17:748-756.
5. Nie, D., K. Tang, C. Diglio, and K. V. Honn. 2000. Eicosanoid regulation of angiogenesis: role of endothelial arachidonate 12-lipoxygenase. *Hemost. Thromb. Vasc. Biol.* 95:2304-2311.
6. Stoltz, R. A., N. G. Abraham, and M. L. Schwartzman. 1996. The role of NF-kB in the angiogenic response of coronary microvessel endothelial cells. *Proc. Natl. Acad. Sci. USA* 93:2832-2837.
7. Hla, T., A. Ristimäki, S. Appleby, and J. G. Barriocanal. 1993. Cyclooxygenase gene expression in inflammation and angiogenesis. *Ann. N.Y. Acad. Sci.* 696:197-204.
8. Jones, M. K., H. Wang, B. M. Peskar, E. Levin, R. M. Itani, I. J. Sarfeh, and A. S. Tarnawski. 1999. Inhibition of angiogenesis by nonsteroidal anti-inflammatory drugs: Insight into mechanisms and implications for cancer growth and ulcer healing. *Nature Med.* 5:1418-1423.
9. Marcus, A. J. 1995. Aspirin as prophylaxis against colorectal cancer *N. Engl. J. Med.* 333, no. September 7:656-658.
10. Vane, J. 2000. Aspirin and other anti-inflammatory drugs. *Thorax* 55 (Suppl. 2):S3.

11. Clària, J., and C. N. Serhan. 1995. Aspirin triggers previously undescribed bioactive eicosanoids by human endothelial cell-leukocyte interactions. *Proceedings of the National Academy of Sciences of the United States of America* 92, no. 21:9475-9479.
12. Chiang, N., T. Takano, C. B. Clish, N. A. Petasis, H.-H. Tai, and C. N. Serhan. 1998. Aspirin-triggered 15-epi-lipoxin $A_4$ (ATL) generation by human leukocytes and murine peritonitis exudates: Development of a specific 15-epi-$LXA_4$ ELISA. *J. Pharmacol. Exp. Ther.* 287:779-790.
13. Clish, C. B., J. A. O'Brien, K. Gronert, G. L. Stahl, N. A. Petasis, and C. N. Serhan. 1999. Local and systemic delivery of a stable aspirin-triggered lipoxin prevents neutrophil recruitment in vivo. *Proc. Natl. Acad. Sci. USA* 96:8247-8252.
14. Serhan, C. N. 1997. Lipoxins and novel aspirin-triggered 15-epi-lipoxins (ATL): a jungle of cell-cell interactions or a therapeutic opportunity? *Prostaglandins* 53:107-137.
15. Marshall, N. J., C. J. Goodwin, and S. J. Holt. 1995. A critical assessment of the use of microculture tetrazolium assays to measure cell growth and function. *Growth Regulation* 5:69-84.
16. Colville-Nash, P. R., C. A. S. Alam, I. Appleton, J. R. Brown, M. P. Seed, and D. A. Willoughby. 1995. The pharmacological modulation of angiogenesis in chronic granulomatous inflammation. *J. Pharmacol. Exp. Ther.* 274:1463-1472.
17. Gupta, K., S. Kshirsagar, W. Li, L. Gui, S. Ramakrishnan, P. Gupta, P. Y. Law, and R. P. Hebbel. 1999. VEGF prevents apoptosis of human microvascular endothelial cells via opposing effects on MAPK/ERK and SAPK/JNK signaling. *Exp. Cell Res.* 247:495-504.
18. Eliceiri, B. P., and D. A. Cheresh. 1999. The role of av integrins during angiogenesis insights into potential mechanisms of action and clinical development. *J. Clin. Invest.* 103:1227-1230.
19. Kelavkar, U. P., and K. F. Badr. 1999. Effects of mutant p53 expression on human 15-lipoxygenase-promoter activity and murine 12/15-lipoxygenase gene expression: Evidence that 15-lipoxygenase is a mutator gene. *Proc. Natl. Acad. Sci. USA* 96:4378-4383.
20. Munger, K. A., A. Montero, M. Fukunaga, S. Uda, T. Yura, E. Imai, Y. Kaneda, J. M. Valdivielso, and K. F. Badr. 1999. Transfection of rat kidney with human 15-lipoxygenase suppresses inflammation and preserves function in experimental glomerulonephritis. *Proc. Natl. Acad. Sci. USA* 96:13375-13380.
21. Gronert, K., T. Martinsson-Niskanen, S. Ravasi, N. Chiang, and C. N. Serhan. 2001. Selectivity of recombinant human leukotriene $D_4$, leukotriene $B_4$, and lipoxin $A_4$ receptors with aspirin-triggered 15-epi-$LXA_4$ and regulation of vascular and inflammatory responses. *Am. J. Pathol.* 158:3-9.
22. Sodin-Semrl, S., B. Taddeo, D. Tseng, J. Varga, and S. Fiore. 2000. Lipoxin $A_4$ inhibits IL-1 beta-induced IL-6, IL-8, and matrix metalloproteinase-3 production in human synovial fibroblasts and enhances synthesis of tissue inhibitors of metalloproteinases. *J. Immunol.* 164:2660-2666.
23. Clària, J., M. H. Lee, and C. N. Serhan. 1996. Aspirin-triggered lipoxins (15-epi-LX) are generated by the human lung adenocarcinoma cell line (A549)-neutrophil interactions and are potent inhibitors of cell proliferation. *Molecular Medicine* 2:583-596.
24. McMahon, B., C. Stenson, F. McPhillips, A. Fanning, H. R. Brady, and C. Godson. 2000. Lipoxin $A_4$ antagonizes the mitogenic effects of leukotriene $D_4$ in human renal mesangial cells: Differential activation of MAP kinases through distinct receptors. *J. Biol. Chem.* 275:27566-27575.
25. Chiang, N., K. Gronert, F.-H. Qiu, and C. N. Serhan. 2000. Lipoxin $A_4$ receptor. In Cytokine Reference. J. J. Oppenheim, M. Feldmann, S. K. Durum, T. Hirano, J. Vilcek and N. A. Nicola, editors. Academic Press, London. 2219-2233.
26. Takano, T., S. Fiore, J. F. Maddox, H. R. Brady, N. A. Petasis, and C. N. Serhan. 1997. Aspirin-triggered 15-epi-lipoxin $A_4$ and $LXA_4$ stable analogs are potent inhibitors of acute inflammation: Evidence for anti-inflammatory receptors. *J. Exp. Med.* 185:1693-1704.
27. Cotran, R. S., V. Kumar, and T. Collins, editors. 1999. *Robbins Pathologic Basis of Disease*. 6th ed. W.B. Saunders Co., Philadelphia.
28. Masferrer, J. L., A. Koki, and K. Seibert. 1999. COX-2 inhibitors: a new class of antiangiogenic agents. *Ann. N.Y. Acad. Sci.* 889:84-86.
29. Gewirtz, A. T., B. McCormick, A. S. Neish, N. A. Petasis, K. Gronert, C. N. Serhan, and J. L. Madara. 1998. Pathogen-induced chemokine secretion from model intestinal epithelium is inhibited by lipoxin $A_4$ analogs. *J. Clin. Invest.* 101:1860-1869.
30. Hachicha, M., M. Pouliot, N. A. Petasis, and C. N. Serhan. 1999. Lipoxin (LX)$A_4$ and aspirin-triggered 15-epi-$LXA_4$ inhibit tumor necrosis factor 1a-initiated neutrophil responses and trafficking: regulators of a cytokine-chemokine axis. *J. Exp. Med.* 189:1923-1929.

Those skilled in the art will know, or be able to ascertain, using no more than routine experimentation, many equivalents to the specific embodiments of the invention described herein. These and all other equivalents are intended to be encompassed by the following claims. All publications and references cited herein, including those in the background section, are expressly incorporated herein by reference in their entirety.

What is claimed is:

1. A method to increase vascular or endothelial cellular proliferation in a subject in need of wound healing comprising the step of administering to the subject in need of wound healing, an effective amount of an $LXB_4$ compound or pharmaceutically acceptable salts, esters, and amides thereof wherein the $LXB_4$ compound is selected from 14-epi-$LXB_4$, 15-epi-$LXB_4$ and 15-epi-$LXB_4$-acetylenic such that vascular or endothelial cellular proliferation in the subject in need of wound healing is increased.

* * * * *